US008173131B2

(12) United States Patent
Tripp et al.

(10) Patent No.: US 8,173,131 B2
(45) Date of Patent: May 8, 2012

(54) COMPOSITIONS AND METHODS FOR MODULATING RSV INFECTION AND IMMUNITY

(75) Inventors: Ralph A. Tripp, Decatur, GA (US); Les Jones, Peachtree City, GA (US); Larry J. Anderson, Atlanta, GA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

(21) Appl. No.: 11/139,372

(22) Filed: May 26, 2005

(65) Prior Publication Data

US 2006/0018925 A1     Jan. 26, 2006

Related U.S. Application Data

(62) Division of application No. 10/420,387, filed as application No. PCT/US01/32459 on Oct. 18, 2001, now abandoned.

(60) Provisional application No. 60/241,521, filed on Oct. 18, 2000.

(51) Int. Cl.
*A61K 39/42* (2006.01)
*A61K 39/155* (2006.01)
*A61K 38/04* (2006.01)
*A61K 38/16* (2006.01)

(52) U.S. Cl. ............... 424/159.1; 514/3.7; 424/211.1
(58) Field of Classification Search ............... 424/204.1, 424/211.1; 530/300
See application file for complete search history.

(56) References Cited

U.S. PATENT DOCUMENTS 6,113,911 A    9/2000  Binz et al.

FOREIGN PATENT DOCUMENTS

| CA | 2257943 | 12/1997 |
|---|---|---|
| CA | 2302833 | 3/1999 |
| WO | WO-PCT/US97/00293 | 1/1997 |
| WO | WO 97 46581 A | 12/1997 |
| WO | WO 99 14334 A | 3/1999 |

OTHER PUBLICATIONS

Corbeil, et al., Involvement of the complement system in the protection of mice from challenge with respiratory syncytial virus Long strain following passive immunization with monoclonal antibody 18A2B2, Vaccine, vol. 14, Issue 6, , Apr. 1996, pp. 521-525.*
Wathen MW, J Gen Virol. Oct. 1989;70 ( Pt 10):2625-35. Related Articles, Links Characterization of a novel human respiratory syncytial virus chimeric FG glycoprotein expressed using a baculovirus vector.*
Wathen et al., J Infect Dis. Mar. 1991;163(3):477-82.Vaccination of cotton rats with a chimeric FG glycoprotein of human respiratory syncytial virus induces minimal pulmonary pathology on challenge.*
Murphy et al., Virus Research 1994 vol. 32 pp. 13-36.*
Tripp et al Nature Immunology 2001 vol. 2, No. 8 pp. 732-738 (from IDS).*
Feng et al., Kidney International 1999 vol. 56, pp. 612-620.*
Anderson et al. Antigenic characterization of respiratory syncytial virus strains with monoclonal antibodies. *J. Infect. Dis.* 15:626-633 (1985).
Beisser et al. Human cytomegalovirus chemokine receptor gene US28 is transcribed in latently infected THP-1 monocytes. *J. Virol.* 75:5949-5957 (2001).
Bourgeois et al. Heparin-like structures on respiratory syncytial virus are involved in its infectivity in vitro. *J. Virol.* 72(9):7221-7227 (1998).
Boyden. The chemotactic effect of mixtures of antibody and antigen on polymorphonuclear leukocytes. *J. Exp. Med.* 115:453-466 (1962).
Brake et al. Alpha-factor-directed synthesis and secretion of mature foreign proteins in *Saccharomyces cerevisiae*. PNAS 82:4642-4646 (1984).
Bright et al. Comparison of the T helper cell response induced by respiratory syncytial virus and its fusion protein in BALB/c mice. *Vaccine* 13:915-922 (1995).
Chanock et al. Serious respiratory tract disease caused by respiratory syncytial virus: prospects for improved therapy and effective immunization. *Pediatrics* 90:137-143 (1992).
Chin et al. Field evaluation of a respiratory syncytial virus vaccine and a trivalent parainfluenza virus vaccine in a pediatric population. *Am. J. Epidemiol.* 89(4):449-463 (1969).
Combadiere et al. Gene cloning, RNA distribution, and functional expression of mCX3CR1, a mouse chemotactic receptor for the CX3C chemokine fractalkine. *Bio. & Biophys. Res. Comm.* 253:728-732 (1998).
Combadiere et al. Identification of CX3CR1. A chemotactic receptor for the human CX3C chemokine fractalkine and a fusion coreceptor for HIV-1. *J. Biol. Chem.* 273:23799-23804 (1998).
Connors et al. Respiratory syncytial virus (RSV) F, G, M2 (22K), and N proteins each induce resistance to RSV challenge, but resistance induced by M2 and N proteins is relatively short-lived. *J. Virol.* 65:1634-1637 (1991).
Crowe et al. Recombinant human respiratory syncytial virus (RSV) monoclonal antibody Fab is effective therapeutically when introduced directly into the lungs of RSV-infrected mice. *Proc Natl Acad Sci USA* 91:1386-90 (1994).

(Continued)

*Primary Examiner* — Mary E Mosher
*Assistant Examiner* — Myron Hill
(74) *Attorney, Agent, or Firm* — Gifford, Krass, Sprinkle, Anderson & Citkowski, P.C.

(57) ABSTRACT

Compositions and methods are provided for the treatment or prevention of RSV disease by modulating RSV infection and immunity. In particular, amino acid sequences in the RSV G glycoprotein, containing the chemokine motif defined as C-X-X-X-C (or CX3C), are identified that are essential in causing RSV infection and disease. The chemokine motif is biologically active and participates in virus binding to and infection of susceptible cells. The prevention or treatment of RSV infection is achieved by interfering with the motif, such as by administering a vaccine in which the motif is altered or by administration or induction of blocking molecules that inhibit the biological activity of the motif.

9 Claims, 12 Drawing Sheets

OTHER PUBLICATIONS

Driscoll. Macrophage inflammatory proteins: biology and role in pulmonary inflammation. *Exp. Lung Res.* 20:473-490 (1994).

Endres et al. The Kaposi's sarcoma-related herpes virus (KHSV)-encoded chemokine vMIP-1 is a specific agonist for the CC chemokine receptor (CCR)8. *J. Exp. Med.* 189:1993-1998 (1999).

Feldman et al. Identification of a linear heparin binding domain for human respiratory syncytial virus attachment glycoprotein G. *J.Virol.* 73:6610-6617 (1999).

Feldman et al. The fusion glycoprotein of human respiratory syncytial virus facilitates virus attachment and infectivity via an interaction with cellular heparin sulfate. *J. Virol.* 74:6442-6447 (2000).

Fixler. Respiratory syncytial virus infection in children with congenital heart disease: a review. *Ped. Cardiol.* 17:163-168 (1996).

Fong et al. Fractalkine and CX3CR1 mediate a novel mechanism of leukocyte capture, firm adhesion, and activation under physiologic flow. *J. Exp. Med.* 188:1413-1419 (1998).

Graham et al. Priming immunization determines T helper cytokine mRNA expression patterns in lungs of mice challenged with respiratory syncytial virus. *J. Immunol.* 151:2032-2040 (1993).

Groothuis et al. Safety and immunogenicity of a purified F protein respiratory syncytial virus (PFP-2) vaccine in seropositive children with bronchopulmonary dysplasia. *J. Infect. Dis.* 177:467-469 (1998).

Hall. Respiratory syncytial virus: a continuing culprit and conundrum. *J. Ped.* 135:2-7 (1999).

Hallak et al. Iduronic acid-containing glycosaminoglycans on target cells are required for efficient respiratory syncytial virus infection. *Virol.* 271:264-275 (2000).

Hancock et al. Generation of atypical pulmonary inflammatory responses in BALB/c mice after immunization with the native attachment (G) glycoprotein of respiratory syncytial virus. *J. Virol.* 70:7783-7791 (1996).

Johnson et al. Priming with secreted glycoprotein G of respiratory syncytial virus (RSV) augments interleukin-5 production and tissue eosinophilia after RSV challenge. *J. Virol.* 72:2871-2880 (1998).

Johnson et al. The G glycoprotein of human respiratory syncytial viruses of subgroups A and B: extensive sequence divergence between antigenically related proteins. *Proc. Nat. Acad. Sci. USA* 84:5625-5629 (1987).

Jones et al. Replacing the complementarity-determning regions in a human antibody with those from a mouse. *Nature* 321:522-525 (1986).

Karron et al. Respiratory syncytial virus (RSV) SH and RSV G glycoproteins are not essential for viral replication in vitro: clinical evaluation and molecular characterization of a cold-passaged, attenuated RSV subgroup B mutant. *Proc. Nat. Acad. Sci. USA* 94:13961-13966 (1997).

Kearney et al. A New Mouse Myeoma Cell Line that has Lost Immunoglobulin Expression but Permits the Construction of Antibody-Secreting Hybrid Cell Lines. *J. Immunol.* 123(4):1548-1550 (1979).

Koopmann et al. Structure and function of the glycosaminoglycan binding site of chemokine macrophage-inflammatory protein-1 beta. *J. Immunol.* 163:2120-2127 (1999).

Kurt-Jones et al. Pattern recognition receptors TLR4 and CD14 mediate response to respiratory syncytial virus. *Nature Immunol.* 1:398-401 (2000).

Lalani et al. The purified myxoma virus gamma interferon receptor homolog M-T7 interacts with the heparin-binding domains of chemokines. *J. Virol.* 71:4356-4363 (1997).

Loetscher et al. Chemokines and their receptors in lymphocyte trafficking and HIV infection. *Adv. Immunol.* 74:127-180 (2000).

Martinez et al. Antigenic structure of the human respiratory syncytial virus G glycoprotein and relevance of hypermutation events for the generation of antigenic variants. *J. Gen. Virol.* 78:2419-2429 (1997).

McDermott et al. Chemokines and their receptors in infectious disease. *Springer Sem. Immunopathol.* 22:393-415 (2000).

McIntosh et al. Immunopathologic mechanisms in lower respiratory tract disease of infants due to respiratory syncytial virus. *Prog. Med. Viro.* 26:94-118 (1980).

Melero et al. Antigenic structure, evolution and immunobiology of human respiratory syncytial virus attachment (G) protein. *J. Gen. Virol.* 75:2411-2418 (1997).

Michieli et al. Inhibition of oncogene-mediated transformation by ectopic expression of $p21^{Waf1}$ in NIH3T3 cells. *Oncogene* 12:775-784 (1996).

Olmsted et al. Expression of the F glycoprotein of respiratory syncutial virus by a recombinant vaccinia virus: comparison of the individual contributions of the F and G glycoproteins to host immunity. *Proc. Nat. Acad. Sci. USA* 83:7462-7466 (1986).

Openshaw. Immunity and immunopathology to respiratory syncytial virus. The mouse model. *Amer. J. Respir. & Crit. Care Med.* 152:859-862 (1995).

Pelchen-Matthews et al. Chemokine receptor trafficking and viral replication. *Immunol. Rev.* 168:33-49 (1999).

Roder et al. Purification of respiratory syncytial virus F and RSV G glycoproteins. *J. Chromat.* 737:97-106 (2000).

Schall. Fractalkine—a strange attractor in the chemokine landscape. *Immunol. Today* 18:147-152 (1997).

Sparer et al. Eliminating a region of respiratory syncytial virus attachment protein allows induction of protective immunity without vaccine-enhanced lung eosinophilia. *J. Exp. Med.* 187:1921-1926 (1998).

Srikiatkhachorn et al. Virus-specific memory and effector T lymphocytes exhibit different cytokine responses to antigens during experimental murine respiratory syncytial virus infection. *J. Virol.* 71:678-685 (1997).

Stott et al. Immune and histopathological responses in animals vaccinated with recombinant vaccine viruses that express individual genes of human respiratory syncytial virus. *J. Virol.* 61:3855-3861 (1987).

Sullender. Antigenic analysis of chimeric and truncated RSV G glycoproteins of respiratory syncytial virus. *Virol.* 209:70-79 (1995).

Tebbey et al. Atypical pulmonary eosinophilia is mediated by a specific amino acid sequence of the attachment (G) protein of respiratory syncytial virus. *J. Exp. Med.* 188:1967-1972 (1998).

Tempest et al. Reshaping a Human Monoclonal Antibody to Inhibit Human Respiratory Syncytial Virus Infection In Vivo. *Biotechnology* 9:266-271 (1991).

Tripp et al. Cytotoxic T-lymphocyte precursor frequencies in BALB/c mice after acute respiratory syncytial virus (RSV) infection or immunization with a formalin-inactivated RSV vaccine. *J. Virol.* 72:8971-8975 (1998).

Tripp et al. Respiratory syncytial virus (RSV) G and/or SH proteins alter Th1 cytokines, natural killer cells and neutrophils responding to pulmonary infection in BALB/c mice. *J. Virol.* 73:7099-7107 (1999).

Tripp et al. Respiratory syncytial virus G and/or SH glycoproteins modify CC and CXC chemokine mRNA expression in the BALB/c mouse. *J. Virol.* 74:6227-6229 (2000).

Tripp et al. Th(1)- and Th(2)-TYPE cytokine expression by activated t lymphocytes from the lung and spleen during the inflammatory respone to respiratory syncytial virus. *Cytokine* 12:801-807 (2000).

Tripp et al. Respiratory syncytial virus infection and G and/or SH protein expression contribute to substance P, which mediates inflammation and enhanced pulmonary disease in BALB/c mice. *J. Virol.* 74:1614-1622 (2000).

Tripp et al. CX3C chemokine mimicry by respiratory syncytial virus G glycoprotein. *Nature Immunology* 2(8):732-738 Abstract (2001).

Weibel et al. Respiratory virus vaccines. V. field evaluation for efficacy of heptavalent vaccine. *Am. Rev. Resp. Dis*. 94:362-379 (1996).
Witt et al. Differential binding of chemokines to glycosaminoglycan subpopulations. *Curr. Biol*. 4:394-400 (1994).
Zhang et al. Expression of respiratory syncytial virus-induced chemokine gene networks in lower airway epithelial cells revealed by cDNA microarrays. *J. Virol*. 75(19):9044-9058 (2001).
Imai, et al., "Identification and Molecular Characterization of Fractalkine Receptor CX3CR1, which Mediates Both Leukodyte Migration and Adhesion", (1997) Cell, vol. 91; 521-530.
Mizoue, et al., "Solution Structure and Dynamics of the CX3C Chemokine Domain of Fractalkine and Its Interaction with an N-terminal Fragment of CX3CR1"; (1999) Biochemistry 38: 1402-1414.

Cane, et al., "Indentification of variable domains of the attachment (G) protein of subgroup A respiratory syncytial viiruses"; (1991) Journal of General Virology 72:2091-2096.

Tripp, et al., "CX3C chemokine mimicry by respiratory syncytial virus G glycoprotein"; (2001) Nature Immunology 2(8): 732-738.

Levine, et al., "Demonstration that Glycoprotein G Is the Attachment Protein of Respiratory Syncytial Virus"; (1987) J. Gen. Virol. 68:2521-2524.

Walsh, et al., "Comparison of Antigenic Sites of Subtype-specifi Respiratory Syncytial Virus Attachment Proteins"; (1989) J. Gen. Virol. 70:2953-2961.

Simard, et al. "Subgroup specific protection of mice from respiratory syncytial virus infection with peptides encompassing the amino acid region 174-157 from the G glycoprotein: the role of cysteinyl residues in protection"; (1997) Vaccine 15:423-432.

Trudel, et al., "Protection of BALBC/C Mice from Respiratory Syncytial Virus Infection by Immunization with a Synthetic Peptide Derived from the G Glycoprotein"; (1991) Virology 185: 749-757.

Norrby, et al., "Site Directed serology with synthetic peptides representing the large glycoprotein G of respiratory syncytial virus"; (1987) PNAS(USA) 84: 6572-6576.

Anderson, et al., "Identification of Epitopes on Respiratory Syncytial Virus Proteins by Competitive Binding Immunoassay"; (1986) Journal of Clinical Microbiology 23(3):475-480.

Akerlind-Stopner, et al., "A Subgroup Specific Antigenic Site in the G Protein of Respiratory Syncytial Virus Forms a Disulfide-Bonded Loop"; (1990) J. Virol. 64(10): 5143-5148.

Plotnicky-Gilquin, et al., "Identification of Multiple Protective Epitopes (Protectopes) in the Central Conserved Domain of a Prototype Human Respiratory Syncytial Virus G Protein"; (1999) J. Virol. 73(7); 5637-5645.

Domachowske and Rosenberg, "Respiratory Syncytial Virus Infection; Immune Response, Immunopathogenesis and Treatment"; (1999) Clinical Microbiology Reviews 12(2): 298-309.

Weltzin, R., "The therapeutic potential of monoclonal antibodies against respiratory syncytial virus"; (1998) Expert Opinion on Investigational Drugs 7(8): 1271-1283.

Zambon, M., "Active and Passive Immunisation against Respiratory Syncytial Virus"; Rev. Med. Virol. 9: 227-236 (1999).

Martinez and Melero, "Enhanced neutralization of human respiratory syncytial virus by mixtures of monoclonal antibodies to the attachment (G) glycoprotein"; (1998) J. Gen. Virol. 79: 2215-2220.

\* cited by examiner

A:

B.

SEQUENCE LISTING

```
<160> NUMBER OF SEQ ID NOS: 16

<210> SEQ ID NO 1
<211> LENGTH: 32
<212> TYPE: PRT
<213> ORGANISM: Artificial Sequence
<220> FEATURE:
<223> OTHER INFORMATION: Note: Description of Artificial Sequence =
      Synthetic Construct

<400> SEQUENCE: 1

Val Pro Cys Ser Ile Cys Ser Asn Asn Pro Thr Cys Trp Ala Ile Cys
1               5                   10                  15

Lys Arg Ile Pro Asn Lys Lys Pro Gly Lys Lys Thr Thr Thr Lys Pro
            20                  25                  30

<210> SEQ ID NO 2
<211> LENGTH: 12
<212> TYPE: PRT
<213> ORGANISM: Artificial Sequence
<220> FEATURE:
<223> OTHER INFORMATION: Note: Description of Artificial Sequence =
      Synthetic Construct

<400> SEQUENCE: 2

Val Pro Cys Ser Ile Cys Ser Asn Asn Pro Thr Cys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Note: Description of Artificial Sequence =
      Synthetic Construct

<400> SEQUENCE: 3

Thr Cys Trp Ala Ile Cys Lys Arg Ile Pro Asn Lys
1               5                   10

<210> SEQ ID NO 4
<211> LENGTH: 12
```

```
<212> TYPE: PRT
<213> ORGANISM: Artificial Sequence
<220> FEATURE:
<223> OTHER INFORMATION: Note:  Description of Artificial Sequence =
      Synthetic Construct

<400> SEQUENCE: 4

Asn Lys Lys Pro Gly Lys Lys Thr Thr Thr Lys Pro
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Note:  Description of Artificial Sequence =
      Synthetic Construct

<400> SEQUENCE: 5

Thr Cys Ala Ala Ala Cys Lys Arg Ile Pro Asn Lys Lys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Note:  Description of Artificial Sequence =
      Synthetic Construct

<400> SEQUENCE: 6

Thr Cys Trp Ala Ala Cys Lys Arg Ile Pro Asn Lys Lys
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Note:  Description of Artificial Sequence =
      Synthetic Construct

<400> SEQUENCE: 7

Thr Cys Asn Ala Ala Cys Lys Arg Ile Pro Asn Lys Lys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Note:  Description of Artificial Sequence =
      Synthetic Construct

<400> SEQUENCE: 8

Thr Cys Asp Ala Ala Cys Lys Arg Ile Pro Asn Lys Lys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Note:  Description of Artificial Sequence =
      Synthetic Construct

<400> SEQUENCE: 9

Thr Cys Asp Ala Ala Ala Cys Lys Arg Ile Pro Asn Lys Lys
1               5                   10
```

```
<210> SEQ ID NO 10
<211> LENGTH: 13
<212> TYPE: PRT
<213> ORGANISM: Artificial Sequence
<220> FEATURE:
<223> OTHER INFORMATION: Note: Description of Artificial Sequence =
      Synthetic Construct

<400> SEQUENCE: 10

Thr Cys Met Ala Ala Cys Lys Arg Ile Pro Asn Lys Lys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Note: Description of Artificial Sequence =
      Synthetic Construct

<400> SEQUENCE: 11

Thr Cys Phe Ala Ala Cys Lys Arg Ile Pro Asn Lys Lys
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Note: Description of Artificial Sequence =
      Synthetic Construct

<400> SEQUENCE: 12

Cys Trp Ala Ile Cys
1               5

<210> SEQ ID NO 13
<211> LENGTH: 6
<212> TYPE: PRT
<213> ORGANISM: Artificial Sequence
<220> FEATURE:
<223> OTHER INFORMATION: Note: Description of Artificial Sequence =
      Synthetic Construct

<400> SEQUENCE: 13

Cys Trp Ala Ile Ala Cys
1               5

<210> SEQ ID NO 14
<211> LENGTH: 4
<212> TYPE: PRT
<213> ORGANISM: Artificial Sequence
<220> FEATURE:
<223> OTHER INFORMATION: Note: Description of Artificial Sequence =
      Synthetic Construct

<400> SEQUENCE: 14

Cys Trp Ala Cys
1

<210> SEQ ID NO 15
<211> LENGTH: 11
<212> TYPE: PRT
<213> ORGANISM: Artificial Sequence
<220> FEATURE:
<223> OTHER INFORMATION: Note: Description of Artificial Sequence =
      Synthetic Construct
```

```
<400> SEQUENCE: 15

Thr Cys Trp Ala Cys Lys Arg Ile Pro Asn Lys
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Note:  Description of Artificial Sequence =
      Synthetic Construct

<400> SEQUENCE: 16

Thr Cys Trp Ala Ile Ala Cys Lys Arg Ile Pro Asn Lys
1               5                   10
```

COMPOSITIONS AND METHODS FOR MODULATING RSV INFECTION AND IMMUNITY

This application is a divisional application of U.S. patent application Ser. No. 10/420,387, filed Apr. 18, 2003 now abandoned, which is the National Stage of International Application No. PCT/US01/32459 filed on Oct. 18, 2001, which claims benefit of U.S. Provisional Application No. 60/241,521, filed on Oct. 18, 2000 all of which are incorporated herein in their entireties by this reference.

This invention was made at the Centers for Disease Control and Prevention. Therefore, the United States Government has certain rights in this invention.

FIELD OF THE INVENTION

The invention relates generally to the fields of immunology and virology and relates more particularly to methods and compositions for modulating or preventing respiratory syncytial virus infection.

BACKGROUND OF THE INVENTION

Respiratory syncytial virus (RSV) has long been recognized as the major viral pathogen of the lower respiratory tract of infants. It has also been implicated in lower respiratory tract disease in adults, especially the elderly and the immunocompromised. RSV is a high priority for vaccine development but efforts to develop a vaccine have so far failed. The failure in developing a vaccine has led to renewed interest in the pathogenesis of disease and the immune mechanisms surrounding protection.

RSV was first identified as the agent that causes chimpanzee coryza in 1956 and was subsequently isolated from children with pulmonary disease. Today, according to World Health Organization (WHO) estimates, a third of the 12.2 million annual deaths in children under the age of five are due to acute infections of the lower respiratory tract. *Streptococcus pneumoniae, Haemophilus influenzae,* and RSV are the predominant pathogens causing these infections. Of these pathogens, RSV has been described as the single, most important cause of serious respiratory tract infections in infants and young children.

RSV epidemics are seasonal, although the virus likely persists within communities. Peak infection rates occur during cold seasons in temperate climates. The virus affects about 90% of infants and young children by the age two. Most often, infection occurs in infants between the ages of six weeks and six months, with the highest incidence in children under three months of age. Previous infection does not prevent repeated infections that are common in all age groups. For example, in a study in Houston, Tex., infection rates were 68.8 per 100 child-years in infancy, and 82.6 per 100 child-years in the second year of life. In a study in Sweden, antibodies to RSV were produced in 87% of children by age 18 months, and in virtually all children by age three.

RSV may also be the cause of up to 5% of community-acquired lower respiratory tract infections in adults. In the elderly, RSV infection can be especially serious, with up to 10% of hospitalized cases leading to death.

RSV most commonly causes an upper respiratory tract infection. Rhinitis, cough, and sometimes fever characterize such infections. Acute otitis media occurs in up to one third of children with RSV illness. Both RSV and bacterial pathogens have been isolated from the middle ears of children with RSV. RSV also causes croup but the most common serious manifestations of infection are bronchiolitis and pneumonia in children. Signs of upper-respiratory tract involvement commonly precede those of the lower respiratory tract (bronchiolitis and pneumonia) by a few days, and fever, when present, is usually low grade. Death can occur in around 1% of children hospitalized with RSV infection, with the greatest risk of serious complications of infection occurring in children (and adults) with compromised cardiac, pulmonary, or immune function. In adults, RSV can cause exacerbation of chronic obstructive lung disease and congestive heart failure.

The RSV genome comprises a single strand of negative sense RNA that is 15,222 nucleotides in length and yields eleven major proteins. (Falsey, A. R., and E. E. Walsh, 2000, Respiratory syncytial virus infection in adults, *Clinical Microbiological Reviews* 13:371-84.) Two of these proteins, the F (fusion) and G (attachment) glycoproteins, are the major surface proteins and the most important for inducing protective immunity. The SH (small hydrophobic) protein, the M (matrix) protein, and the M2 (22 kDa) protein are associated with the viral envelope but do not induce a protective immune response. The N (major nucleocapsid associated protein), P (phosphoprotein), and L (major polymerase protein) proteins are found associated with virion RNA. The two non-structural proteins, NS 1 and NS2, presumably participate in viral replication but are not present in infectious virions.

RSV infects through the upper respiratory tract (particularly the nasopharynx) and the eyes. The virus has an incubation period of about three to five days. Infections with RSV occur annually in the first few years of life. Thus, the protective immunological response is incomplete. Local secretory IgA is believed to contribute to resistance to infection in the upper respiratory tract. Protection of the lower respiratory tract is mediated partly by serum IgG. The F and G surface glycoproteins are the only RSV proteins known to induce protective neutralizing antibodies. The G glycoprotein appears to play a role in both induction of protective immunity and disease pathogenesis. For example, studies in mice have shown that the G glycoprotein primes for a Th2 CD4$^+$ T cell response, characterized by production of IL-4, IL-5, IL-13 and pulmonary eosinophilia. Eosinophil recruitment and activation are promoted by several factors, such as IL-4 and IL-5. Pulmonary eosinophilia is associated with significant to severe lung pathology and is presumably, in part, mediated by RSV G glycoprotein-induced Th2 CD4$^+$ cells. Expression of G glycoprotein during acute infection in mice has been associated with a modified innate immune response characterized by decreased Th1 cytokine expression (e.g., IL-2 and gamma interferon), altered chemokine mRNA expression (e.g., MIP-1 alpha, MIP-1 beta, MIP-2, IP-10, MCP-1), and decreased NK cell trafficking to the infected lung.

Human RSV strains have been classified into two major groups, A and B. The G glycoprotein has been shown to be the most divergent among RSV proteins. Variability of the RSV G glycoprotein between and within the two RSV groups is believed to be important to the ability of RSV to cause yearly outbreaks of disease. The G glycoprotein comprises 289-299 amino acids (depending on RSV strain), and has an intracellular, transmembrane, and highly glycosylated stalk structure of 90 kDa, as well as heparin-binding domains. The glycoprotein exists in secreted and membrane-bound forms.

Cellular immunity appears to play a prominent role in recovery from RSV infection. Thus, individuals with cellular immunodeficiency (inherited or acquired) have more severe and long-lasting RSV infections than normal individuals. After RSV infection, normal children show an RSV-specific lymphocyte proliferation, which suggests T cell stimulation.

An RSV-specific cytotoxic T lymphocyte response has also been described and is likely to be important to recovery from illness. Both CD4 and CD8 T lymphocyte subsets are involved in terminating RSV replication during infection. The same cytotoxic T lymphocyte response may also exacerbate or augment the clinical disease associated with RSV infection. This hypothesis has been used to explain the more severe disease seen with the formalin-inactivated RSV vaccine tested in the early 1960s.

Successful methods of treating RSV infection are currently unavailable. Infection of the lower respiratory tract with RSV is a self-limiting condition in most cases. No definitive guidelines or criteria exist on how to treat or when to admit or discharge infants and children with the disease. Hypoxia, which can occur in association with RSV infection, can be treated with oxygen via a nasal cannula. Mechanical ventilation for children with respiratory failure, shock, or recurrent apnea can lower mortality. Some physicians prescribe steroids. However, several studies have shown that steroid therapy does not affect the clinical course of infants and children admitted to the hospital with bronchiolitis. Thus corticosteroids, alone or in combination with bronchodilators, may be useless in the management of bronchiolitis in otherwise healthy unventilated patients. In infants and children with underlying cardiopulmonary diseases, such as bronchopulmonary dysphasia and asthma, steroids have also been used.

Ribavirin, a guanosine analogue with antiviral activity, has been used to treat infants and children with RSV bronchiolitis since the mid 1980s, but many studies evaluating its use have shown conflicting results. In most centers, the use of ribavirin is now restricted to immunocompromised patients and to those who are severely ill.

The severity of RSV bronchiolitis has been associated with low serum retinol concentrations, but trials in hospitalized children with RSV bronchiolitis have shown that vitamin A supplementation provides no beneficial effect. Therapeutic trials of 1500 mg/kg intravenous RSV immune globulin or 100 mg/kg inhaled immune globulin for RSV lower-respiratory-tract infection have also failed to show substantial beneficial effects.

In developed countries, the treatment of RSV lower-respiratory-tract infection is generally limited to symptomatic therapy. Antiviral therapy is usually limited to life-threatening situations due to its high cost and to the lack of consensus on efficacy. In developing countries, oxygen is the main therapy (when available), and the only way to lower mortality is through prevention.

Vaccination against RSV is, therefore, the preferred method for reducing RSV-related morbidity. A formalin-inactivated RSV vaccine, tested in the 1960s, was found to be immunogenic, with high rates of seroconversion. However, vaccinated children were found to lack protection from subsequent RSV infection. Furthermore, RSV naive infants who received the formalin-inactivated RSV vaccine, and who were naturally infected with RSV later, developed more severe disease than did a control group immunized with a trivalent parainfluenza vaccine. This experience has necessitated a very cautious approach to testing non-live virus vaccines in RSV naive infants.

However, the formalin-inactivated RSV vaccine failed to cause enhanced disease in older, previously infected children. In addition, studies in BALB/c mice suggest that prior live virus infection predisposes an individual for a safe immune response to non-live vaccines. Consequently, non-live vaccines are being tested in older children and adults previously infected with RSV. Non-live vaccines tested thus far appear to be safe in older children and adults, but their efficacy is unknown. It is hoped that, with new immunologic tools, researchers will be able to understand the pathogenesis of enhanced disease and use this information to design non-live virus vaccines that will be safe in the RSV naive individual.

Efforts toward developing a vaccine for infants and young children are now focused on live virus vaccines. A number of candidate vaccines have been tested in humans, but none have been shown to be sufficiently safe to be considered a viable vaccine for administration to young children.

Therefore, there is a need for safe and effective vaccines against RSV, especially for infants and children. There is also a need for therapeutic agents and methods for treating RSV infection at all ages and in immunocompromised individuals. There is also a need for scientific methods to characterize the protective immune response to RSV so that the pathogenesis of the disease can be studied, and screening for therapeutic agents and vaccines can be facilitated. The present invention overcomes previous shortcomings in the art by providing methods and compositions effective for modulating or preventing RSV infection.

SUMMARY OF THE INVENTION

Compositions and methods are provided for the treatment or prevention of RSV disease by modulating RSV infection and immunity. In particular, amino acid sequences in the RSV G glycoprotein are identified herein that are essential in causing RSV infection and disease. These amino acid sequences contain a chemokine motif, defined as C-X-X-X-C (or CX3C), that is both biologically active (i.e., acts as a CX3C chemokine) and participates in virus binding to, and infection of, susceptible cells. In this motif, C is a cysteine residue and X is any amino acid residue. Each of the three X residues can be a different amino acid or the same amino acid, but not cysteine. The chemokine motif is found at amino acid positions 182-186 of the native RSV G glycoprotein. The CX3C motif binds to the CX3C receptor (CX3CR1) on the surface of human and animal cells.

The compositions and methods provided herein utilize the newly acquired knowledge of the biological and structural importance of the CX3C motif to infect cells, modify immunity, and cause disease, to prevent or inhibit RSV disease. Basically, immunity and treatment are achieved by 1) altering the CX3C motif in a wild type virus in such a way that the virus cannot use it to attach to and infect cells or modulate the host response to viral infection, and using the virus containing the altered motif as a live virus vaccine; 2) enhancing induction of antibodies that block RSV G glycoprotein binding to CX3CR1 or the biological activity associated with RSV G glycoprotein binding to CX3CR1 by a non-live virus vaccine; 3) blocking the activity of the CX3C motif by binding drugs, antibodies, peptides, polypeptides or other blocking molecules to the motif of an infecting virus; 4) inactivating the CX3C site by binding drugs antibodies, peptides, polypeptides or other blocking molecules proximal to the CX3C motif of an infecting virus (preferably the binding of blocking molecules proximal to the motif occurs in regions that alter the secondary structure of the motif, thereby changing biological activity, or that sterically prevent RSV G glycoprotein binding to CX3CR1 or the biological activity associated with RSV G glycoprotein binding to CX3CR1 by a non-live virus vaccine); and/or 5) using assays that detect blocking of RSV G glycoprotein binding to the CX3C receptor (CX3CR1) or that detect blocking of the activity initiated by RSV G glycoprotein binding to CX3CR1 to identify drugs, antibodies, peptides, polypeptides or other blocking molecules antibodies that can be used as RSV antiviral or vaccines that can be safe and effective for preventing RSV disease.

In the present invention, live RSV vaccines are produced by modifying the RSV G glycoprotein CX3C motif to render it nonfunctional for viral attachment and infection of host cells. Preferred RSV vaccines are engineered by making deletion or insertion mutations in the CX3C motif in a live RSV virus.

Another aspect of this invention provides live or non-live RSV vaccines which are produced, or existing live or non-live RSV vaccines which are improved, by modifying the RSV G glycoprotein CX3C motif or proximal regions thereof so that, when the vaccines are administered to a human or animal, higher titers of antibodies are produced that block the biological function of the CX3C motif on the G glycoproteins of subsequently-infecting RSV viruses.

In another aspect of this invention live and non-live RSV vaccines are provided which when administered to a human or animal, induce the production of antibodies that block the biological function of the CX3C motif on the G glycoprotein of subsequently-infecting RSV viruses. Alternatively, the vaccine comprises one or more G glycoprotein peptides or polypeptides from different RSV strains having the foregoing ability.

Also provided is a method for improving or identifying drugs, antibodies, peptides, polypeptides or other blocking molecules that can be used to treat RSV disease and/or as vaccines to prevent RSV disease.

Immunization is achieved by administering to a human or animal an immunogenic amount of one or more of the vaccine compositions of this invention in a pharmaceutically acceptable carrier. RSV treatment is provided by administration of an effective amount of a CX3C blocking molecule in a pharmaceutically acceptable carrier to a RSV infected human or animal. By "pharmaceutically acceptable" is meant a material that is not biologically or otherwise undesirable, i.e., the material may be administered to an individual along with the selected agent without causing any undesirable biological effects or interacting in a deleterious manner with any of the other components of the pharmaceutical composition in which it is contained. A blocking molecule is defined herein as a drug, chemical compound, antibody, peptide, polypeptide or other molecule that blocks the biological activity of the CX3C motif, or blocks the binding of the CX3C G glycoprotein to the CX3C G glycoprotein receptor, which can be the CX3CR1 receptor.

Monoclonal antibodies which are specific for the RSV G glycoprotein CX3C motif or for the receptor to which the CX3C motif binds (particularly the CX3CR1 receptor), or that can be shown to block binding or the activity associated with binding to the CX3CR1 receptor of many or all RSV strains are useful for the treatment of patients with RSV infection. These antibodies are also used prophylactically to prevent patients who are at risk from acquiring RSV.

Polyclonal antibodies, concentrated sera or immunoglobulin preparations containing high titers of antibodies specific for the RSV G glycoprotein CX3C motif or for the receptor to which the CX3C motif binds or that can be shown to block binding or the activity associated with binding to the CX3CR1 receptor of many or all RSV strains are also useful for the treatment or prevention of RSV disease.

The administration of antibodies, peptides, polypeptides or related molecules which block the chemokine-like effects of the CX3C motif of the G glycoprotein on cell migration or activation is also useful for treatment of RSV infection.

It is therefore an object of the present invention to provide vaccines and other pharmaceutical compositions for the prevention, reduction and treatment of RSV disease, wherein the compositions interfere with the biological activity of the RSV G glycoprotein CX3C motif or the binding of the motif to its receptor on host cells.

It is another object of the present invention to provide a method for treating or preventing RSV infection.

It is another object of the present invention to provide a method for treating or preventing bronchiolitis, an upper respiratory infection or a lower respiratory tract infection caused by RSV infection.

It is another object of the present invention to provide a safe and effective vaccine against RSV, especially suited for use in infants and the elderly and other groups at risk for RSV disease.

It is another object of this invention to provide assays that can be used to screen candidate vaccines or antivirals to identify those likely to be safe and effective in treating and/or preventing RSV infection.

These and other objects, features and advantages of the present invention will become apparent after a review of the following detailed description of the disclosed embodiments and the appended claims.

DETAILED DESCRIPTION OF THE INVENTION

Figure 1:
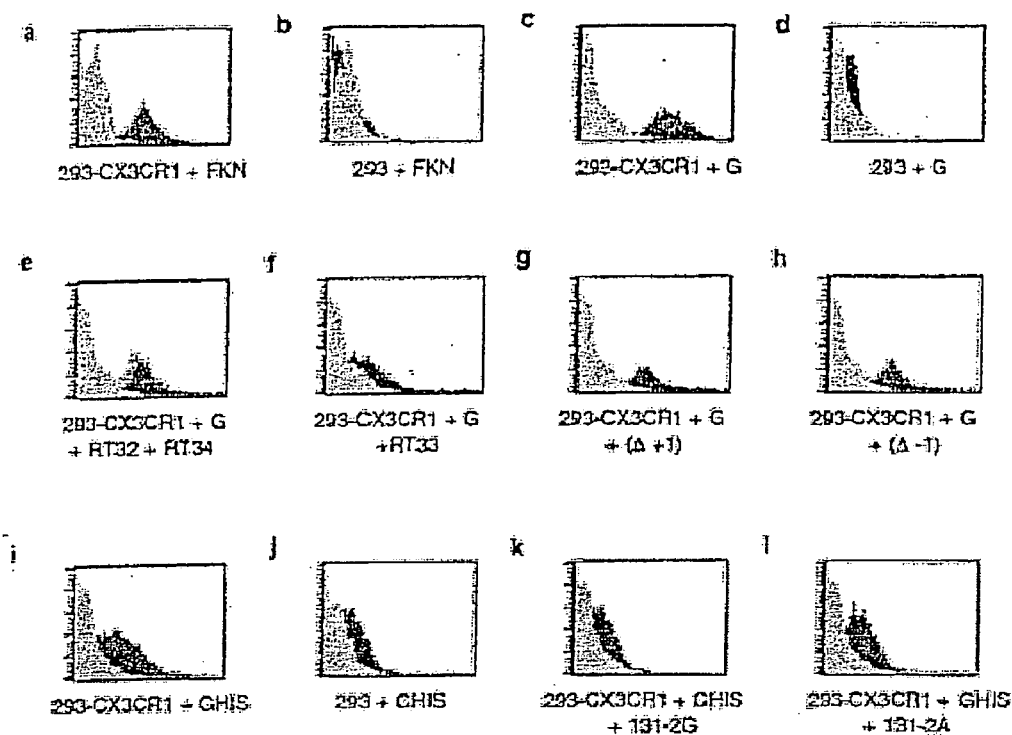
FIGS. 1A-L show G glycoprotein (G), recombinant polyhistidine G glycoprotein ($G_{HIS}$) and Fkn binding to 293-CX3CR1 and 293 cells in the presence and absence of G glycoprotein peptides RT32, RT33, RT34, Δ+1 and Δ−1 and anti-G glycoprotein (131-2G) and anti-F glycoprotein (131-2A) monoclonal antibodies, as determined by flow cytometry. Shown are histogram profiles for 10 nM G glycoprotein, $G_{HIS}$ or Fkn binding to CX3CR1-293 and 293 cells. The dark histograms represent cells stained with a control antibody. The light histograms represent cells stained with biotinylated anti-G glycoprotein cocktail (130-2G, 131-2G) or anti-Fkn antibody (51637.11). The percent positive staining of Fkn or G glycoprotein for a representative experiment is shown: a) 88% Fkn staining of CX3CR1-293 cells; B) 8% Fkn staining of 293 cells; C) 84% G glycoprotein staining of CX3CR1-293 cells; D) 16% G glycoprotein staining of 293 cells; E) 72% staining of G glycoprotein in the presence of peptide RT32 and 74% staining of in the presence of peptide RT34 of CX3CR1-293 cells; F) 48% staining of G glycoprotein in the presence of peptide RT33 of CX3CR1-293 cells; G) 65% staining of G glycoprotein in the presence of peptide Δ+1; H) 73% staining of G glycoprotein in the presence of peptide Δ−1; 1) 68% $G_{HIS}$ staining of CX3CR1-293 cells; J) 12% $G_{HIS}$ staining of 293 cells; K) 10% $G_{HIS}$ staining of CX3CR1-293 cells in the presence of anti-G glycoprotein monoclonal antibody (131-2G); and L) 60% $G_{HIS}$ staining of CX3CR1-293 cells in the presence of anti-F glycoprotein monoclonal antibody (131-2A).

The present invention may be understood more readily by reference to the following detailed description of the preferred embodiments of the invention and the Examples included herein.

Before the present compounds and methods are disclosed and described, it is to be understood that this invention is not limited to specific proteins, specific methods, or specific nucleic acids, as such may, of course, vary. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly dictates otherwise.

Compositions and methods for the treatment or prevention of RSV disease by modulating RSV infection and immunity are described herein. In particular, amino acid sequences in the RSV G glycoprotein, referred to herein as the C-X-X-X-C (or CX3C) chemokine motif, are identified that are essential in causing RSV infection and disease. The CX3C chemokine motif is located at amino acid positions 182-186 in a conserved, proline-rich region of the RSV G glycoprotein molecule. The administration of one or more compositions that directly or indirectly interfere with or block the normal activity or binding of this motif is useful for immunization against and treatment of RSV disease and is also useful for studying the pathology of RSV for the development and screening of therapeutic compositions and treatment strategies.

Chemokines mediate leukocyte trafficking in inflammatory responses and are often produced under pathological conditions such as viral infection. Chemokines are defined as having four conserved cysteines and are divided into subfamilies based upon the motif formed by the first two cysteines. For example, the CXC chemokines have the first two cysteines separated by one amino acid, whereas the first two cysteines are adjacent for CC chemokines. The C chemokines form a third disulfide bridge in addition to the usual two disulfide bridges, and the CX3C chemokines have the first two cysteines separated by three amino acids.

The chemokine motif of RSV G glycoprotein located at amino acid positions 182-186 is a C-X-X-X-C (or CX3C) motif. The motif is biologically active (i.e., it acts as a CX3C chemokine) and it participates in virus binding to, and infection of, susceptible cells. In this motif, C is a cysteine residue and X is any amino acid residue. Each of the three X residues can be a different amino acid or the same amino acid, but not cysteine. The CX3C motif binds to the CX3C receptor (CX3CR1) on the surface of human and animal cells, thereby facilitating RSV infection of the cells.

The compositions and methods described herein provide immunity against and treatment of RSV infection in several ways by directly or indirectly interfering with the normal function or structure of the CX3C motif. The compositions include live or non-live RSV viruses, or fragments thereof, in which the CX3C motif has been altered, and also include blocking molecules that inhibit the function of the CX3C motif.

For example, live RSV virus vaccines are produced by altering the CX3C motif in a wild type virus in such a way that the virus cannot use it to attach to and infect cells or modulate the host response to viral infection. The virus containing the altered motif is administered as a live virus vaccine to induce an immune response that confers subsequent protection against RSV infection.

Drugs, antibodies, peptides, polypeptides or other blocking molecules that bind to and thereby block the normal activity of the G glycoprotein CX3C motif of an infecting RSV virus are administered to treat RSV infection. The CX3C site is also inactivated by binding drugs, antibodies, peptides, polypeptides or other blocking molecules proximal to the CX3C motif of an infecting RSV virus in such a way that the normal activity of the motif is inhibited or compromised. The preferred antibodies do not specifically recognize the CX3C domain, thus limiting the possibility of inducing autoimmunity to structurally similar endogenous chemokines, such as fractalkine.

The normal biological activities of the live, wild-type RSV virus that are inhibited, terminated or modulated by the compositions and methods provided herein include but are not limited to, chemotaxis, cell migration and virus adherence to cells.

RSV Vaccines

In the present invention, live RSV vaccines are produced by modifying the RSV G glycoprotein CX3C motif to render it nonfunctional for viral attachment and infection of host cells. Preferred RSV vaccines are engineered by introducing or selecting for deletion, insertion and/or substitution mutations in the amino acid sequence of the CX3C motif in a live RSV virus. Especially preferred vaccines contain variations from the native amino acid sequence (amino acids 182-186 of the RSV G glycoprotein genome, such as (CWAIC) (SEQ ID NO: 12) to add an additional residue (such as CWAIAC) (SEQ ID NO: 13) or to delete a residue (such as CWAC) (SEQ ID NO: 14). Alternatively, the CX3C motif is altered to delete one or both C residues or by increasing or decreasing the number of X residues between the C residues.

Also provided by this invention are live RSV vaccines that are produced, or existing live RSV vaccines that are improved, by modifying the RSV G glycoprotein CX3C motif or proximal amino acid residues or other parts of the G glycoprotein so that, when administered to a human or animal, higher titers of antibodies are produced that block the biological function of the CX3C motif on the G glycoproteins of subsequently-infecting RSV viruses. "Higher titer" means an antibody titer which is greater than an antibody titer previously detected upon immunization with existing live RSV vaccines.

In another aspect of the invention, live and non-live RSV vaccines are provided that, when administered to a human or animal, induce the production of antibodies that block the biological function of the CX3C motif on the G glycoprotein of subsequently-infecting RSV viruses. For example, the vaccine can comprise one or more G glycoprotein fragments, G glycoprotein peptides or polypeptides from different RSV strains, G glycoproteins from non-live virus vaccines, or G glycoproteins from a live virus vaccine, such as an RSV infectious clone, that, when administered to a human or animal, induce the production of antibodies that inhibit CX3C biological function, such as binding to the CX3C receptor or RSV plaque formation in monolayers of susceptible cells or G glycoprotein-induced leukocyte migration. The RSV infectious clone is available from several sources such as the National Institutes of Health (Dr. Brian Murphy) or from Aviron Corporation (Mountain View, Calif.). Alternatively, the vaccine can comprise one or more G glycoprotein peptides or polypeptides from different RSV strains having the foregoing ability.

Immunization is achieved by administering to a human or animal an immunogenic amount of one or more of the vaccine compositions of this invention in a pharmaceutically acceptable carrier.

RSV Blocking Molecules

RSV treatment is provided by administration, to an RSV infected human or animal, of an effective amount of a CX3C blocking molecule in a pharmaceutically acceptable carrier. A blocking molecule is defined herein as a drug, chemical compound, antibody, peptide, polypeptide or other molecule that blocks the biological activity of the CX3C motif or blocks the binding of the CX3C G glycoprotein to the CX3C G glycoprotein receptor, which is most preferably the CX3CR1 receptor.

Monoclonal antibodies, specific for the RSV G glycoprotein CX3C motif or for the receptor to which the CX3C motif binds (particularly the CX3CR1 receptor) or for other parts of the RSV G glycoprotein such that they block RSV G glycoprotein binding to CX3CR1 or the activity associated with RSV G glycoprotein binding to CX3CR1 for all RSV strains, are useful, in conjunction with neutralizing monoclonal antibodies, to treat patients with disease or to use prophylactically to prevent RSV infection in subjects who are at risk of acquiring RSV disease.

Polyclonal antibodies, concentrated sera or immunoglobulin preparations containing high titers of antibodies specific for the RSV G glycoprotein CX3C motif or for the receptor to which the CX3C motif binds are also useful for treatment or prevention of RSV disease.

The administration of antibodies, peptides, polypeptides or related molecules which block the chemokine-like effects of the CX3C motif of the G glycoprotein on cell migration or activation is also useful for RSV treatment and prevention.

Isolated, recombinant or synthetic proteins or peptides containing the CX3C motif of the RSV G glycoprotein, or active fragments thereof or fusion proteins thereof, can be utilized as blocking molecules as described above, but are also useful as scientific research tools to identify and produce other blocking molecules, thereby promoting an understanding of the mechanisms of RSV viral pathology and the development of antiviral therapies. Furthermore, the isolated, recombinant or synthetic proteins, or antigenic portions thereof (including epitope-bearing fragments), or fusion proteins thereof can be administered to animals as immunogens or antigens, alone or in combination with an adjuvant, for the production of antisera reactive with the CX3C motif. In addition, the proteins can be used to screen antisera from hyperimmune patients from whom antibodies having a very high affinity for the proteins can be derived.

Preferred proteins, peptides or polypeptides of this invention contain the CX3C motif. Most preferably, the proteins, peptides or polypeptides contain the CX3C motif and all or a biologically active or immunogenic portion of the amino acid sequence VPCSICSNNPTCWAICKRIPNKKPGKKTTTKP (SEQ ID NO: 1).

Alternatively the proteins, peptides or polypeptides of this invention contain the CX3C motif and all or a biologically active or immunogenic portion of the amino acid sequence VPCSICSNNPTC (referred to herein as RT32) (SEQ ID NO: 2), TCWAICKRIPNK ((referred to herein as RT33) (SEQ ID NO: 3), NKKPGKKTTTKP (referred to herein as RT34) (SEQ ID NO: 4), or combinations thereof. Other peptides that can be used as blocking molecules include, but are not limited to, TCAAACKRIPNKK (SEQ ID NO: 5), TCWAACKRIPNKK (SEQ ID NO: 6), TCNAACKRIPNKK (SEQ ID NO: 7), TCDAACKRIPNKK (SEQ ID NO: 8), TCDAAACKRIPNKK (SEQ ID NO: 9), TCMAACKRIPNKK (SEQ ID NO: 10), TCFAACKRIPNKK (SEQ ID NO: 1). The methods described in the examples herein were utilized to demonstrate that these peptides 1) inhibit >90% of RSV infection of susceptible cells (e.g., Vero cells), 2) inhibit >90% of G glycoprotein CX3C binding to CX3CR1, 3) inhibit RSV plaque formation and 4) inhibit RSV infection in vivo.

The present invention also provides isolated nucleic acids encoding the RSV G glycoprotein peptides of the present invention and fragments thereof. These nucleic acids can be used to produce the peptides of this invention or as nucleic acid vaccines, wherein the peptides of this invention are produced in a subject.

A nucleic acid as used herein refers to single- or double-stranded molecules which may be DNA, comprised of the nucleotide bases A, T, C and G, or RNA, comprised of the bases A, U (substitutes for T), C, and G. The nucleic acid may represent a coding strand or its complement. Nucleic acids may be identical in sequence to the sequence which is naturally occurring or may include alternative codons which encode the same amino acid as that which is found in the naturally occurring sequence. Furthermore, nucleic acids may include codons which represent conservative substitutions of amino acids as are well known in the art.

As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

The nucleic acid encoding the peptide or polypeptide of this invention can be part of a recombinant nucleic acid construct comprising any combination of restriction sites and/or functional elements as are well known in the art which facilitate molecular cloning and other recombinant DNA manipulations. Thus, the present invention further provides a recombinant nucleic acid construct comprising a nucleic acid encoding a peptide and/or polypeptide of this invention.

The present invention further provides a vector comprising a nucleic acid encoding a peptide and/or polypeptide of this invention. The vector can be an expression vector which contains all of the genetic components required for expression of the nucleic acid in cells into which the vector has been introduced, as are well known in the art. The expression vector can be a commercial expression vector or it can be constructed in the laboratory according to standard molecular biology protocols. The expression vector can comprise viral nucleic acid including, but not limited to, vaccinia virus, adenovirus, retrovirus and/or adeno-associated virus nucleic acid. The nucleic acid or vector of this invention can also be in a liposome or a delivery vehicle which can be taken up by a cell via receptor-mediated or other type of endocytosis.

The nucleic acid of this invention can be in a cell, which can be a cell expressing the nucleic acid whereby a peptide and/or polypeptide of this invention is produced in the cell. In addition, the vector of this invention can be in a cell, which can be a cell expressing the nucleic acid of the vector whereby a peptide and/or polypeptide of this invention is produced in the cell. It is also contemplated that the nucleic acids and/or vectors of this invention can be present in a host animal (e.g., a transgenic animal) which expresses the nucleic acids of this invention and produces the peptides and/or polypeptides of this invention.

The nucleic acid encoding the peptides and polypeptides of this invention can be any nucleic acid that functionally encodes the peptides and polypeptides of this invention. To functionally encode the peptides and polypeptides (i.e., allow the nucleic acids to be expressed), the nucleic acid of this invention can include, for example, expression control sequences, such as an origin of replication, a promoter, an enhancer and necessary information processing sites, such as ribosome binding sites, RNA splice sites, polyadenylation sites and transcriptional terminator sequences.

Preferred expression control sequences are promoters derived from metallothionine genes, actin genes, immunoglobulin genes, CMV, SV40, adenovirus, bovine papilloma virus, etc. A nucleic acid encoding a selected peptide or polypeptide can readily be determined based upon the genetic code for the amino acid sequence of the selected peptide or polypeptide and many nucleic acids will encode any selected peptide or polypeptide. Modifications in the nucleic acid sequence encoding the peptide or polypeptide are also contemplated. Modifications that can be useful are modifications to the sequences controlling expression of the peptide or polypeptide to make production of the peptide or polypeptide inducible or repressible as controlled by the appropriate inducer or repressor. Such methods are standard in the art (49). The nucleic acid of this invention can be generated by means standard in the art, such as by recombinant nucleic acid techniques and by synthetic nucleic acid synthesis or in vitro enzymatic synthesis.

The present invention also provides a method for producing the peptides and polypeptides of this invention comprising producing the cells of this invention which contain the nucleic acids or vectors of this invention as exogenous nucleic acid; culturing the cells under conditions whereby the exogenous nucleic acid in the cell can be expressed and the encoded peptide and/or polypeptide can be produced; and isolating the peptide and/or polypeptide from the cell. Thus, it is contemplated that the peptides and polypeptides of this invention can be produced in quantity in vitro in either prokaryotic or eukaryotic expression systems as are well known in the art.

For expression in a prokaryotic system, there are numerous E. coli (Escherichia coli) expression vectors known to one of ordinary skill in the art useful for the expression of nucleic acid which encodes peptides or polypeptides. Other microbial hosts suitable for use include bacilli, such as Bacillus subtilis, and other enterobacteria, such as Salmonella, Serratia, as well as various Pseudomonas species. These prokaryotic hosts can support expression vectors which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence and have ribosome binding site sequences for example, for initiating and completing transcription and translation. If necessary, an amino terminal methionine can be provided by insertion of a Met codon 5' and in-frame with the polypeptide. Also, the carboxy-terminal extension of the polypeptide can be removed using standard oligonucleotide mutagenesis procedures.

The nucleic acid sequences can be expressed in hosts after the sequences have been positioned to ensure the functioning of an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired nucleic acid sequences (50).

For eukaryotic system expression, a yeast expression system can be used. There are several advantages to yeast expression systems. First, evidence exists that polypeptides produced in a yeast expression system exhibit correct disulfide pairing. Second, post-translational glycosylation is efficiently carried out by yeast expression systems. The Saccharomyces cerevisiae pre-pro-alpha-factor leader region (encoded by the MFα-1 gene) is routinely used to direct protein secretion from yeast (51). The leader region of pre-pro-alpha-factor contains a signal peptide and a pro-segment which includes a recognition sequence for a yeast protease encoded by the KEX2 gene. This enzyme cleaves the precursor protein on the carboxyl side of a Lys-Arg dipeptide cleavage-signal sequence. The polypeptide coding sequence can be fused in-frame to the pre-pro-alpha-factor leader region. This construct is then put under the control of a strong transcription promoter, such as the alcohol dehydrogenase I promoter or a glycolytic promoter. The coding sequence is followed by a translation termination codon, which is followed by transcription termination signals. Alternatively, the coding sequence of interest can be fused to a second polypeptide coding sequence, such as Sj26 or β-galactosidase, used to facilitate purification of the resulting fusion polypeptide by affinity chromatography. The insertion of protease cleavage sites to separate the components of the fusion polypeptide is applicable to constructs used for expression in yeast.

Efficient post-translational glycosylation and expression of recombinant polypeptides can also be achieved in Baculovirus systems in insect cells, as are well known in the art.

The nucleic acids of this invention can also be expressed in mammalian cells to produce the peptides and polypeptides of this invention. Mammalian cells permit the expression of peptides and polypeptides in an environment that favors important post-translational modifications such as folding and cysteine pairing, addition of complex carbohydrate structures and secretion of active protein. Vectors useful for the expression of peptides and polypeptides in mammalian cells are characterized by insertion of the coding sequence between a strong viral promoter and a polyadenylation signal. The vectors can contain genes conferring either gentamicin or methotrexate resistance for use as selectable markers. For example, the coding sequence can be introduced into a Chinese hamster ovary (CHO) cell line using a methotrexate resistance-encoding vector. Presence of the vector RNA in transformed cells can be confirmed by Northern blot analysis and production of a cDNA or opposite strand RNA corresponding to the peptide or polypeptide coding sequence can be confirmed by Southern and Northern blot analysis, respectively. A number of other suitable host cell lines capable of producing exogenous peptides and polypeptides have been developed in the art and include the CHO cell lines, HeLa cells, myeloma cell lines, Jurkat cells and the like. Expression vectors for these cells can include expression control sequences, as described above.

The nucleic acids and/or vectors of this invention can be transferred into the host cell by well-known methods, which vary depending on the type of cell host. For example, calcium chloride transfection is commonly utilized for prokaryotic cells, whereas calcium phosphate treatment or electroporation may be used for other cell hosts.

The nucleic acids encoding the peptides and polypeptides of this invention can also be administered as nucleic acid vaccines. For the purposes of vaccine delivery, a nucleic acid encoding a peptide or polypeptide of this invention can be in an expression vector that can comprise viral nucleic acid including, but not limited to, vaccinia virus, adenovirus, retrovirus and/or adeno-associated virus nucleic acid. The nucleic acid or vector of this invention can also be in a liposome or a delivery vehicle which can be taken up by a cell via receptor-mediated or other type of endocytosis. The nucleic acid vaccines of this invention can be in a pharmaceutically acceptable carrier or administered with an adjuvant. The nucleic acids encoding the peptides and polypeptides of this invention can also be administered to cells in vivo or ex vivo.

Antibodies generated against the peptides of this invention and isolated from antisera of this invention are useful for blocking the binding of the CX3C motif or as research tools. The terms "antibody" and "antibodies" as used herein include monoclonal antibodies, polyclonal, chimeric, single chain, bispecific, simianized, and humanized antibodies, as well as Fab fragments, including the products of an Fab immunoglobulin expression library. The term "antigen" refers to RSV G glycoprotein or any portion of the G glycoprotein that binds CX3C or a G glycoprotein peptide which can induce an immune response in a mammal.

As described above, the antibodies provided herein can be monoclonal or polyclonal, preferably a F(ab)'2 fragment lacking the Fc portion of the antibody. The antibodies can be prepared by generating B cell hybridomas, as described in more detail below, or by using laboratory animals such as mouse, humanized mouse, rat, rabbit or goat which are immunized with the peptides and/or polypeptides of this invention. The peptides' and/or polypeptides can contain deletion, insertion and/or substitution mutations in the G glycoprotein that encompass part of or all of amino acids 182-186 of the RSV G glycoprotein or the intact RSV G glycoprotein, a portion of the RSV G glycoprotein, or a modified RSV G glycoprotein can be used for immunization. Screening can then be carried out to identify antibodies that block RSV G glycoprotein binding to CX3CR1 or block the activities induced by RSV G glycoprotein binding to CX3CR1. To enhance the antibody response, immune adjuvant or modifiers may be included as described in more detail below. Especially preferred are vaccines consisting of variations of the CWAIC (SEQ ID NO: 12) amino acid sequence that add an additional residue(s) (e.g., CWAIAC) (SEQ ID NO: 13) and/or delete a residue(s) (e.g., CWAC) (SEQ ID NO: 14) from the CXXXC motif defined by the CWAIC (SEQ ID NO: 12) amino acid sequence (e.g., 182-186). The vaccine can also comprise the portions of the G glycoprotein proximal to the CX3C motif. In addition, the CX3C motif can be altered in a variety of ways, including but not limited to, deleting one or both cysteine ("C") residues or increasing or decreasing the number of residues ("X") between the cysteine residues.

Monoclonal antibodies are generated by methods well known to those skilled in the art. The preferred method is a modified version of the method of Kearney et al. (52), which is incorporated by reference in its entirety herein. Briefly, animals such as mice or rabbits are inoculated with the immunogen in adjuvant, and spleen cells are harvested and mixed with a myeloma cell line. The cells are induced to fuse by the addition of polyethylene glycol. Hybridomas are chemically selected by plating the cells in a selection medium containing hypoxanthine, aminopterin and thymidine (HAT). Hybridomas are subsequently screened for the ability to produce monoclonal antibodies that block RSV G glycoprotein binding to CX3CR1 and/or modulate biological activity associated with RSV G glycoprotein binding to CX3CR1. Hybridomas producing antibodies are cloned, expanded and stored frozen for future production.

Techniques for the production of single chain antibodies are known to those skilled in the art and described in U.S. Pat. No. 4,946,778 and can be used to produce single chain antibodies to the motifs described herein. Phage display technology may be used to select antibody genes having binding activities for the CX3C motif, from PCR-amplified v genes of lymphocytes from humans screened for having antibodies to the CX3C motif or naive libraries.

The antibodies of this invention are useful for blocking RSV G glycoprotein binding to CX3CR1 or for modulating the biological activity associated with RSV G glycoprotein binding to CX3CR1 by a non-live virus vaccine or for passive immunization. Preferably, the antibody is modified so that it is less immunogenic in the patient to whom it is administered. For example, if the patient is a human, the antibody may be "humanized" by transplanting the complementarity determining regions of the hybridoma-derived antibody into a human monoclonal antibody as described by Jones et al. (53).

Polyclonal antibodies are prepared by screening human blood donors and selecting those that have high titer antibodies that block RSV G glycoprotein binding to CX3CR1 or block the activities induced by RSV G glycoprotein binding to CX3CR1 as well as antibodies that have other important biologic functions, e.g., neutralizing antibodies. Polyclonal antibodies can also be obtained by immunizing donors with vaccines that induce antibodies that block RSV G glycoprotein binding to CX3CR1 or block the activities induced by RSV G glycoprotein binding to CX3CR1, and/or have other important biologic functions, e.g., neutralizing antibodies. Serum from the selected donors is then pooled and made into immunoglobulin preparations.

Screening Assays

Assays are provided to screen vaccines and drugs, chemical compounds, antibodies, peptides, polypeptides or other molecules for the ability to block RSV G glycoprotein binding to CX3CR1 or to block the activities induced by RSV G glycoprotein binding to CX3CR1. Assays of this invention include those 1) that detect the ability to neutralize RSV virus not neutralized by heparin; 2) that detect the ability to block binding of the RSV G glycoprotein to cells transfected with the CX3CR1 receptor; or 3) that detect the ability to block RSV G glycoprotein-mediated migration of leukocytes.

Immunological and Pharmaceutical Compositions

Immunological compositions, including the vaccines described above, and other pharmaceutical compositions containing the modified live RSV or non-live RSV or the CX3C-containing RSV G glycoproteins, polypeptides, peptides or antibodies are included within the scope of the present invention. One or more of these compositions can be formulated and packaged, alone or in combination, using methods and materials known to those skilled in the art for vaccines. The immunological response may be used therapeutically or prophylactically and may provide antibody immunity or cellular immunity such as that produced by T lymphocytes such as cytotoxic T lymphocytes or $CD4^+$ T lymphocytes.

The immunological compositions, such as vaccines, and other pharmaceutical compositions can be administered alone or in any combination to treat or protect against infections caused by RSV. In particular, the compositions can be used to protect humans against bronchiolitis, an upper respiratory infection or a lower respiratory tract infection caused by RSV infection.

To enhance immunogenicity, the CX3C-containing RSV G glycoproteins, polypeptides or peptides of this invention can be conjugated to a carrier molecule. Suitable immunogenic carriers include proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein derived or non-protein derived substances are known to those skilled in the art. An immunogenic carrier typically has a molecular weight of at least 1,000 daltons, and preferably of greater than 10,000 daltons. Carrier molecules often contain a reactive group to facilitate covalent conjugation to the hapten. The carboxylic acid group or amine group of amino acids or the sugar groups of glycoproteins are often used in this manner. Carriers lacking such groups can often be reacted with an appropriate chemicals to produce them. Preferably, an immune response is produced when the immunogen is injected into animals such as humans, mice, rabbits, rats, goats, sheep, guinea pigs, chickens, and other animals, most preferably mice and rabbits. Alternatively, a multiple antigenic peptide comprising multiple copies of the protein or polypeptide, or an antigenically or immunologically equivalent polypeptide may be sufficiently antigenic to improve immunogenicity without the use of a carrier.

The CX3C-containing RSV G glycoproteins, polypeptides or peptides or intact RSV RSV G glycoprotein, RSV G glycoprotein polypeptides or peptides or modifications of the RSV G glycoprotein that induce antibodies that block RSV G glycoprotein binding to CX3CR1 or block the activities induced by RSV G glycoprotein binding to CX3CR1 may be administered with an adjuvant in an amount effective to enhance the immunogenic response. At this time, the only adjuvant widely used in humans has been alum (aluminum phosphate or aluminum hydroxide). Saponin and its purified component Quil A, Freund's complete adjuvant and other adjuvants used in research and veterinary applications have toxicities which limit their potential use in human vaccines. However, chemically defined preparations such as muramyl dipeptide, monophosphoryl lipid A, phospholipid conjugates, encapsulation of the conjugate within a proteoliposome, and encapsulation of the protein in lipid vesicles may also be useful.

Methods of Administration and Dose of Pharmaceutical Compositions

Methods for treating individuals diagnosed with RSV disease and conditions associated with RSV infection, such as bronchiolitis, upper respiratory infection, and lower respiratory infection by administering the compositions described above are also provided in this invention.

Also provided by this invention is a method of treating or preventing an RSV infection in a subject comprising administering to the subject an effective amount of RSV G glycoprotein peptide, polypeptide, molecule antibody or peptide-encoding nucleic acid of this invention that alters the biological activity of the CX3C motif of the G glycoprotein of RSV and an anti-viral composition. The anti-viral compositions can include small drug-like molecule inhibitors of RSV replication and infection: nucleoside analogs such as ribavarin, EICAR, Pyrazofurin, 3-deazaguanine, GR92938X and LY253963. These inhibitors are targeted to inhibit inosine monophosphate dehydrogenase (IMPDH). Inhibitors targeted to inhibit virus adsorption and entry are also useful. Prominent among this class are polyoxometalates and CL387626 (Wyeth-Ayerst, Pearl River, N.Y.). Other examples of polyoxometalates are T118, Trimeris' benzathrone, BABIM and RD30028. Antisense oligonucleotide inhibitors of RSV are also useful, such as V590, an inhibitor that targets residues in RSV NS1/NS2 genes.

The RSV G glycoprotein peptides can be incorporated into a pharmaceutical carrier such as saline, dextrose, water, glycerol, ethanol, other therapeutic compounds, and combinations thereof. The formulation should be appropriate for the mode of administration as described below and may include other immune modifiers such as heparin. The composition may also contain other additional biologically inert ingredients such as flavorants, fillers, etc.

Suitable methods of administration include, but are not limited to, intramuscular, intravenous, intranasal, mucosal, via aerosol delivery or by any route that produces the desired effect of inhibiting the biological activity of the CX3C motif (or domain) in the G glycoprotein. Other nonlimiting examples of such routes of administration include oral, parenteral and transdermal.

A vaccine of this invention can be packaged in a single dosage for immunization by parenteral (i.e., intramuscular, intradermal or subcutaneous) administration or nasopharyngeal (i.e., intranasal) administration. The vaccine is most preferably delivered by inhalation. The vaccine is preferably combined with a pharmaceutically acceptable carrier to facilitate administration. The carrier is usually water or a buffered saline, with or without a preservative. The vaccine may be lyophilized for resuspension at the time of administration or in solution.

Microencapsulation of the vaccine will also give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters polyamides, poly (d,l-lactide-co-glycolide) (PLGA) and other biodegradable polymers.

An effective amount of the compositions of this invention ranges from nanogram/kg to milligram/kg amounts for young children and adult. Based on this range, equivalent dosages for lighter or heavier body weights can be determined. The dose should be adjusted to suit the individual to whom the composition is administered and will vary with age, weight and metabolism of the individual. The vaccine may additionally contain stabilizers such as thimerosal (ethyl(2-mercaptobenzoate-S)mercury sodium salt) (Sigma Chemical Company, St. Louis, Mo.) or physiologically acceptable preservatives. The exact amount of the composition required will vary from subject to subject, depending on the species, age, weight and general condition of the subject, the particular peptide or polypeptide used, its mode of administration and the like. Thus, it is not possible to specify an exact amount for every peptide or polypeptide. However, an appropriate amount can be determined by one of ordinary skill in the art using only routine experimentation given the teachings herein. One skilled in the art will realize that dosages are best optimized by the practicing physician and methods for determining dose amounts and regimens and preparing dosage forms are described, for example, in *Remington's Pharmaceutical Sciences* (47).

As an example, to a subject diagnosed with an RSV infection or known to be at risk of being infected by RSV, between about 50-1000 nM and more preferably, between about 100-500 nM of a composition of this invention can be administered and can be in an adjuvant, at one to three week intervals for approximately 12 weeks or until an evaluation of the subject's clinical parameters (e.g., symptoms and RSV RNA levels indicate that the subject is not infected by RSV). The treatment can be continued or resumed if the subject's clinical parameters indicate that HCV infection is present and can be maintained until the infection is no longer detected by these parameters.

The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Binding Studies

Purified G glycoprotein was examined for binding to 293-CX3CR1 cells[33]. A pcDNA 3.1 plasmid containing the CX3CR1 gene and a neomycin resistance gene was used to stably transfect human embryonic kidney (HEK) cells. Neomycin resistance was used for selection and maintenance of plasmid transfection of human embryonic kidney cells. To confirm transfection, lysates of CX3CR1-transfected human embryonic kidney cells were stained with anti-CX3CR1 antibody in Western blot analysis or intact transfected cells were examined by flow cytometry.

All binding studies were done on ice and either G glycoprotein or human Fkn (R&D Diagnostics, Minneapolis, Minn.) were diluted between 1 nM-100 nM in PBS (GIBCO) containing 1% bovine serum albumin (Sigma) and incubated with the 293-CX3CR1 cells or 293 control cells for 30 min at 4° C. Fractalkine saturated 293-CX3CR1 binding between 1-10 nM. For inhibition studies, 100 pM-1 μM human Fkn or G glycoprotein was preincubated with the cells for 30 min at 4° C. Without washing, 100 pM of either Fkn or G glycoprotein was added and incubated for 30 min at 4° C. The cells were washed, blocked with FcγRIII blocking antibody (HB197) for 30 min on ice, washed and stained as appropriate with either an anti-G glycoprotein monoclonal antibody cocktail (132-5B, 132-5G, 130-2G, 232-IF) or a biotinylated anti-G glycoprotein monoclonal antibody cocktail (130-2G, 131-2G) or anti-Fkn monoclonal antibody (51637.11; R&D Diagnostics). Concentrations of 1 μg of anti-G glycoprotein monoclonal antibody (131-2G)[34], rabbit anti-CX3CR1 sera[33], and anti-CX3CR1 monoclonal antibody containing 10 μg/ml heparin were used in all experiments. The percent inhibition in the absence of heparin for anti-G glycoprotein antibody inhibition of G glycoprotein ranged from 32-48% and 4-10% for Fkn, and anti-CX3CR1 antibody inhibition ranged 40-55% for both G glycoprotein and Fkn. Anti-G glycoprotein antibodies 130-SF and 130-9G, predicted to bind outside of the CX3C motif[35], did not inhibit either G glycoprotein or Fkn (range 4-8%). Staining was detected with absorbed FITC-goat anti-mouse (H & L chain) monoclonal antibody (PharMingen, San Diego, Calif.) or streptavidin-PE (PharMingen) using flow cytometry (FACScan, Becton-Dickinson, Mountain View, Calif.). A 76 amino acid $^{125}$I-Fkn polypeptide comprising the CX3CR domain (NEN, Boston, Mass.) was used in radioligand studies[33]. As a control, the void volume following purified G glycoprotein passaged over an anti-G glycoprotein antibody (130-2G) affinity column was examined by flow cytometry for binding to either 293 or 293-CX3CR1 cells. No G glycoprotein binding to either 293 or 293-CX3CR1 cells was detected by flow cytometry using anti-G monoclonal antibody (131-2G). Inhibition studies using the eluate to compete for G glycoprotein binding to 293 or 293-CX3CR1 cells showed no inhibition, suggesting that G glycoprotein, and not a contaminant, was binding to CX3CR1.

Peptides

For peptide inhibition studies, a series of G glycoprotein peptides were identified in the amino acid sequence of the A2 strain of RSV (GENBANK, attachment protein locus 1912305, Table 4). The peptides were synthesized using a simultaneous, multiple solid-phase peptide synthesis method on a peptide synthesizer (Perkin-Elmer Applied Biosystems, Berkeley, Calif.), and tested for homogeneity by reverse-phase liquid chromatography and capillary electrophoresis (www.biotech.cdc.gov/protein/methods). Inhibition assays were performed as described for the binding studies above.

G Glycoprotein Purification

Two different G glycoprotein preparations were examined in this study: a purified G glycoprotein isolated from RSV/A2 (RSV)-infected Vero cells (ATCC CCL 81; infected at a multiplicity of infection between 0.5 and 1 and harvested between day 4 or 5 pi), and a purified recombinant soluble polyhistidine-tagged G glycoprotein preparation. The purified G glycoprotein isolated from RSV-infected Vero cells was used in this study because this preparation contained the natural form of the G glycoprotein, however, comparable results were achieved using the recombinant soluble polyhistidine-tagged G glycoprotein preparation. The purified G glycoprotein isolated from RSV-infected Vero cells was prepared using a modification of a previously described three-step isolation procedure[44]. Briefly, virus lysate collected by freeze-thawing flasks containing RSV-infected Vero cells was diluted in PBS containing 1 mM PMSF and 2 mM EDTA, sonicated on ice, centrifuged at 100,000 g for 30 min at 10° C., and the pellet collected. The pellet was resuspended in loading buffer (20 mM Tris, 500 mM NaCl, 1 mM PMSF, 2 mM DTT, 2 mM EDTA, 10 mM N-acetyl-glucosamine and 1% Triton X-100, pH 7.5), sonicated on ice, and a cleared lysate collected following centrifugation at 12,500 g for 30 min at 4° C. The viral glycoproteins were captured using a wheat germ lectin-Sepharose 4B column pre-eluted with loading buffer containing 500 mM N-acetyl-glucosamine and equilibrated with loading buffer containing 1% n-octyl-glucopyranoside (n-OG buffer). The G glycoprotein was eluted with loading buffer containing 500 mM N-acetyl-glucosamine and dialyzed against two changes of M-buffer (250 mM sucrose, 25 mM MES-NaOH, 10 mM NaCl, 2 mM EDTA, 1 mM PMSF in n-OG buffer, pH 5.7), and loaded onto a Q-Sepharose anion exchange column pre-eluted with M-buffer containing 2 mM NaCl. The G glycoprotein was eluted using a linear NaCl gradient (from 0.1 M to 1 M) in M-buffer. Fractions eluted with 100 mM and 200 mM NaCl containing the G glycoprotein were dialyzed against two changes of PBS.

Figure 4:
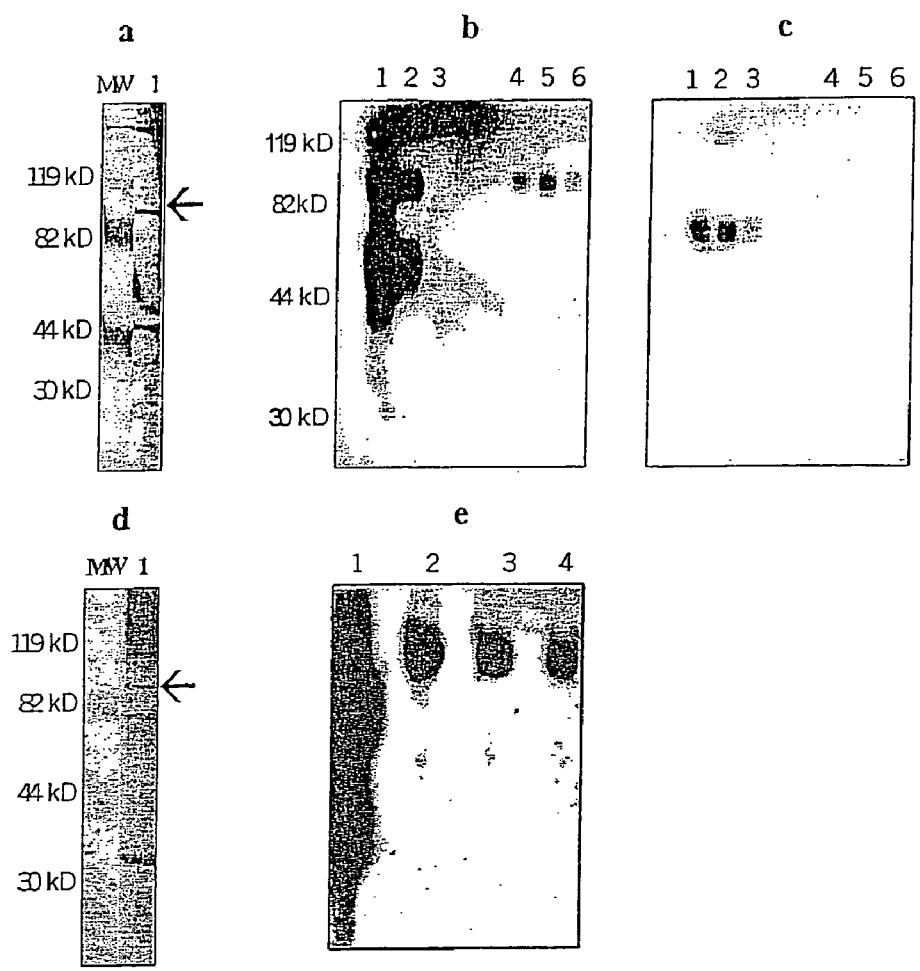
FIGS. 4A-E show the characterization of the G glycoprotein preparations: A) A silver stained non-reduced SDS-PAGE of the G glycoprotein preparation from wheat germ lectin purified RSV-infected Vero cell lysate (Lane 1); (B), (C) Western blot analyses of the sequential fractions collected during the purification procedure and probed with either anti-G glycoprotein monoclonal antibody (131-2A) or anti-F glycoprotein monoclonal antibody (131-2A): Lane 1=unpurified RSV-infected Vero cell lysate, Lane 2=wheat germ lectin column eluate, Lane 3=flow-thru from Q column, Lane 4=100 mM NaCl Q column eluate, Lane 5=200 mM NaCl Q column eluate, Lane 6=300 mM NaCl Q column eluate; D) A silver stained non-reduced SDS-PAGE of the recombinant polyhistidine-tagged G glycoprotein ($G_{HIS}$) preparation: Lane 1=concentrated Ni-NTA affinity column $G_{HIS}$ eluate; E) A Western blot analysis of the $G_{HIS}$ preparation: Lane 1=G glycoprotein preparation from wheat germ lectin purified RSV-infected Vero cell, Lane 2=$G_{HIS}$ lysate from Vero cells stably transfected with pcDNA encoding $G_{HIS}$, Lane 3=flow through from Ni-NTA affinity column, Lane 4=purified $G_{HIS}$ in eluate off Ni-NTA affinity column. MW=molecular weight markers. For silver stained non-reduced SDS-PAGE analysis, an arrow indicates the predicted G glycoprotein.

Purified recombinant polyhistidine-tagged G glycoprotein was prepared from Vero cells stably transfected with pcDNA encoding soluble polyhistidine-tagged G glycoprotein under zeocyin selection. Transfected cells were frozen at −70° C., and the cells were collected in PBS containing 1 mM PMSF, and centrifuged at 1000 g for 10 minutes at 4° C. The pellet was resuspended in Gsol buffer (20 mM Na PO$_4$, 500 mM NaCl, 250 mM sucrose, 1 mM PMSF, 1% Triton X-100, pH 7.5), sonicated on ice, then centrifuged at 12,500 g for 30 min at 4° C. The polyhistidine-tagged G glycoprotein was captured and purified using a HisTrap-Sepharose 4B column (Ni-NTA affinity column) as described by the manufacturer (Amersham Pharmacia Biotech (Piscataway, N.J.). The polyhistidine-tagged G glycoprotein was eluted with Gsol buffer containing 1% nOG buffer and 250 mM imidazole and dialyzed against two changes of PBS. Characterization of the contents of the G glycoprotein preparation was done by gel electrophoresis and Western blot. The wheat germ lectin column fraction enriched for both G and F glycoproteins from RSV-infected Vero cell lysate produced multiple bands by gel electrophoresis and silver stain (FIG. 4). Bands at approximately 90 kD and 45 kD correspond to two bands detected by Western blot with anti-G glycoprotein monoclonal antibody (131-2G)[34] and a band at approximately 70 kD band corresponds to a band detected by Western blot with an anti-F glycoprotein monoclonal antibody (131-2A)[34] (FIG. 4). After the final purification step, i.e., Q-sepharose elution, only the G glycoprotein band was detected by Western blot (FIG. 4), indicating the final G glycoprotein preparation contained no detectable F glycoprotein. The purified recombinant polyhistidine-tagged G glycoprotein recovered from the His-Trap-Sepharose 4B column contained G glycoprotein but no F glycoprotein as detected by Western blot (Panel 4) and other protein bands indicated by gel electrophoresis and silver stain.

In Vivo Examination of Cell Trafficking

Cell trafficking to the lung in naïve and FI-RSV-immune BALB/c mice was examined following intranasal treatment with either 1 μM fractalkine, RSV G glycoprotein or RSV G peptides. All mice were females purchased from Harlan Sprague Dawley (Indianapolis, Ind.) and maintained at the Centers for Disease Control and Prevention in Atlanta, Ga. FI-RSV-immune mice were immunized in the superficial gluteal muscle using 106 pfu equivalents of FI-RSV in accordance with methods known to those skilled in the art. Mice were anesthetized with 2,2,2,-tribromoethanol and intranasally treated with 0.05 ml of either fractalkine, RSV G glycoprotein or peptide diluted in PBS (GIBCO). At day two post-treatment, the mice were anesthetized, exsanguinated by severing the right caudal artery, and the bronchoalveolar (BAL) cells collected in PBS containing 1% BSA (Sigma). BAL cells were blocked with 10% normal mouse sera (Jackson Laboratories, Bar Harbor, Me.) in PBS, and then stained with the appropriate combinations of FITC- or PE-labeled anti-CD3 (145-2C11), anti-CD4 (GK1.5), anti-CD8 (53-6.7), anti-CD11b (M1/70), anti-CD45R/B220 (RA3-6B2), anti-pan NK cell (DX5), anti-neutrophil (RB6-8C5), and mouse isotype Ab controls (all from PharMingen, San Diego, Calif.). The distribution of cell surface markers was determined in two-color mode on a FACScan with CellQUEST software (Becton-Dickinson, Mountain View, Calif.).

Leukocyte Chemotaxis

Leukocyte chemotaxis toward Fkn, G glycoprotein or media was measured according to Boyden[46] using 24 well plates (Costar, Cambridge, Mass.) with 3 μm filter inserts (Nalge Nunc, Rochester, N.Y.) coated with an extracellular matrix consisting primarily of laminin, collagen IV and proteoglycan (ECM, Sigma, St. Louis, Mo.). For murine studies, $5 \times 10^5$ naïve spleen cells was placed in the upper chamber and 10 nM mouse Fkn or 10 nM G glycoprotein, anti-CX3CR1 antibody, anti-G or anti-F glycoprotein monoclonal antibody, normal rabbit sera, rabbit anti-CCR5 sera or media was placed in the upper or lower chamber as appropriate. For human studies, $10^6$ density gradient purified (Lymphocyte Separation Media, ICN Biomedicals, Aurora, Ohio, per manufacture instructions) peripheral blood mononuclear cells (PBMC) from normal human adult donors was placed in the upper chamber in the presence or absence of 1 μM peptide RT33, and 10 nM human Fkn, 10 nM G glycoprotein or 1 μM peptide RT33 placed in the lower chambers. The modified Boyden chamber was incubated at 37° C. for 4-6 h, the inserts removed, washed in PBS (GIBCO BRL), fixed in 3% gluteraldehyde and stained in formalin-buffered 0.01% crystal violet. Chemotactic cells were visualized with a microscope. Chemotactic cells were analyzed for CX3CR1 expression by collecting cells from the upper or lower modified Boyden chambers, antibody staining (2A9-1) and flow cytometry as described. Leucocytes chemotactic toward G or Fkn expressed a higher percent of CX3CR1 in the lower (25-30%) versus upper chamber (7-11%).

RSV Plaque Reduction Assays

Dilutions of Fkn (R&D systems), SDF-1 α (R&D systems), G glycoprotein, heparin (Sigma), G glycoprotein peptides and anti-CX3CR1 antibody were made in serum-free Dulbecco's Modified Eagle's Media (DMEM; GIBCO) containing 1% BSA (Sigma) and preincubated with the Vero cells for 1 h at 37° C. 50 μg of anti-CX3CR1 antibody or heat-inactivated (56° C., 30 min) normal rabbit sera (control) were used in all experiments. Normal rabbit sera had no significant effect on plaque number. Dilutions of RSV were made in serum-free DMEM (GIBCO) and added to pretreated Vero cells for 2 h at 37° C. Following virus infection, DMEM (GIBCO) containing 10% FBS (Hyclone, Logan, Utah) was added to the wells. Plaques were enumerated using immunostaining for F and G glycoproteins using biotinylated monoclonal antibodies 131-2A (anti-F glycoprotein) and 130-2G (anti-G glycoprotein) as described[45].

RNAse Protection Analysis

RNA isolation and multi-probe RNAse protection analysis (RPA) was performed according to the manufacturer (PharMingen, San Diego, Calif.). mRNA was isolated using a Poly (A)Pure kit (Ambron, Austin, Tex.). Vero cells were used for RNA extraction. Total RNA was extracted using RNA STAT-50 LS as described by the manufacturer (TEL-TEST Inc., Friendswood, Tex.). V28 mRNA was detected by RPA using the RiboQuant Multi-Probe RNase Protection Assay System (PharMingen, San Diego, Calif.).

Specificity of G Glycoprotein Binding to CX3CR1

The receptor for Fkn, CX3CR1, was previously identified and characterized using anti-CX3CR1 rabbit antiserum and CX3CR1-transfected human embryonic kidney cells (293-CX3CR1 cells)[33]. Flow cytometry using anti-CX3CR1 rabbit antiserum[33] indicated that the percent of detectable CX3CR1 on 293-CX3CR1 cells increased from 4-10% on untransfected 293 cells to 80-92% for 293-CX3CR1 cells. Fkn binding to 293-CX3CR1 cells peaked and was constant at 100 pM-10 nM, thus 10 nM Fkn was used to calculate the percent of Fkn maximal binding (Fkn-Maximum, Table 1). Examination of a wheat germ lectin column fraction enriched for both G and F glycoproteins (FIG. 4) showed G glycoprotein binding increased from 18% on 293 cells to 70% on 293-CX3CR1 cells while F glycoprotein binding increased from 8% on 293 cells to 12% on 293-CX3CR1 cells. To confirm G glycoprotein bound to 293-CX3CR1 cells, a monoclonal antibody to G glycoprotein[34] was used in an inhibition binding study with a purified recombinant polyhistidine-tagged G glycoprotein (10 nM, Table 2). The anti-G glycoprotein monoclonal antibody (131-2G), which is reactive with a G glycoprotein fragment (amino acids 1-173)[35], inhibited 86 to 92% of G glycoprotein binding to 293-CX3CR1 cells as detected by a panel of anti-G glycoprotein monoclonal antibodies reactive to 3 different antigenic sites on the G glycoprotein[35], but did not inhibit Fkn binding (0-4%). In contrast, anti-G glycoprotein monoclonal antibody 130-2G, reactive with a COOH-terminal domain of the G glycoprotein (amino acids 215-298)[35], and an antibody to F glycoprotein, did not inhibit G glycoprotein (12-20% and 4-12%, respectively) or Fkn (5-10% and 4-10%, respectively) binding to 293-CX3CR1 cells. As expected, recombinant polyhistidine-tagged G glycoprotein binding increased from a range of 7-12% for 293 cells to a range of 68-88% for 293-CX3CR1 cells, and binding to 293-CX3CR1 cells was inhibited (80-88%) by monoclonal antibody 131-2G.

To determine if G glycoprotein bound 293-CX3CR1 cells via CX3CR1, the ability of four reagents (anti-CX3CR1 rabbit antiserum, anti-CX3CR1 monoclonal antibody (2A9-1), Fkn and a 76 amino acid 125-I-Fkn polypeptide containing the CX3C domain) that bind to CX3CR1 to block G glycoprotein binding to 293-CX3CR1 cells was examined. In addition, to determine if binding of G glycoprotein to 293-CX3CR1 cells was dependent upon the CX3C motif, G glycoprotein peptides with a single residue insertion (Δ+1) or deletion (Δ−1) in the CX3C motif and also peptides that lacked or included the CX3C motif (Table 4) were generated. This panel of peptides was analyzed for their ability to block G glycoprotein or Fkn binding to 293-CX3CR1 cells.

Figure 2:
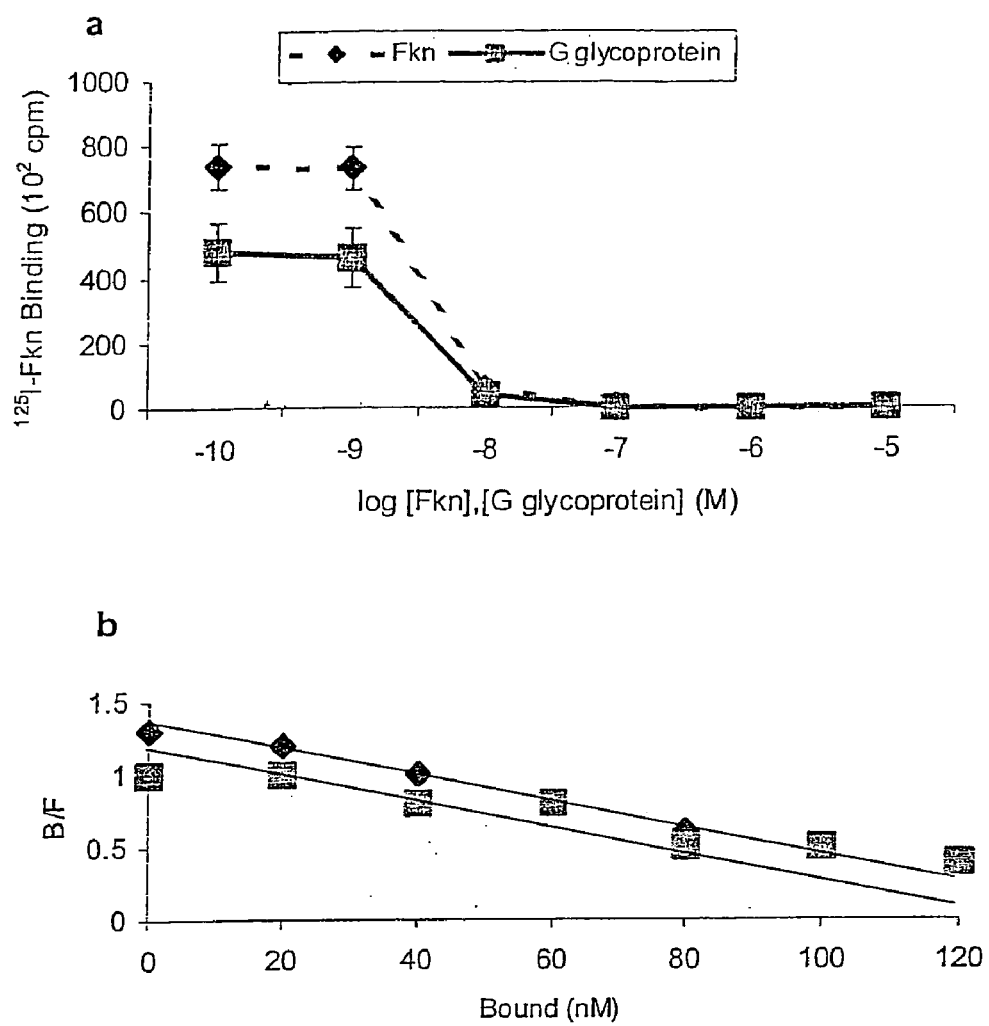
FIGS. 2A-B show 293-CX3CR1 and 293 cells were incubated with 1 nM $^{125}$I-fractalkine comprising the 76 amino acid CX3C chemokine domain, in the presence of increasing amounts of unlabeled Fkn or G glycoprotein for 2 h at 37° C. in the presence of azide. The cell-associated radioactivity was determined: A) The data are the mean±SE of 293 cell-adjusted triplicate measurements representative of three separate experiments; B) Scatchard analysis of the binding data. In three experiments, the mean±SD of the binding parameters were: $K_d$ (Fkn)=5.8±1.4 nM and $K_d$ (G glycoprotein)=2.1±1.6 nM. Non-specific $^{125}$I-fractalkine binding to 293 cells is defined as the total amount of cell-associated radioactivity in the presence of 1000-fold excess of unlabeled Fkn, and was ≤5% of total binding at the concentrations examined.

Since both the G glycoprotein and Fkn can bind to cells via HBD-GAG interactions[22,37,38], heparin was included in these studies to inhibit this (Table 2). G glycoprotein binding to 293-CX3CR1 cells was minimally inhibited (20-34%) by Fkn alone, however the addition of Fkn to heparin almost completely inhibited G glycoprotein binding (from 78-84% to 85-98%). The extensive G glycoprotein HBD-GAG interaction with 293-CX3CR1 cells is not unexpected given the highly glycosylated nature of the G glycoprotein[28]. G glycoprotein binding to 293-CX3CR1 cells in the presence of heparin was also further inhibited by peptide RT33 that contained the CX3C motif (from 78-84% to 85-94%) and by the addition of the two anti-CX3CR1 antibodies (from 78-84% to 88-94%). A similar increase in inhibition of Fkn binding to 293-CX3CR1 cells in the presence of heparin was noted with the addition of G glycoprotein (from 57-65% to 80-85%) or peptide RT33 (from 57-65% to 70-80%) or the two anti-CX3CR1 antibodies (78-84% to 88-97%). The peptides that did not contain the CX3C motif (RT32, RT34) and peptides with changes in the CX3C motif (Δ+1 and Δ−1) (Table 4) as well as control normal rabbit serum did not affect binding. These data suggest that the majority of G glycoprotein binding occurs through HBD-GAG interaction and most of the remaining binding is accounted for by G glycoprotein interaction with CX3CR1. Treatment with 10 nM-10 μM concentrations of different chemokines (MIP-2, IP-10, macrophage inflammatory protein-related protein-1 (C10) and growth regulated oncogene-α, KC) was also unable to alter Fkn or G glycoprotein binding to 293-CX3CR1 cells. Radioligand inhibition studies[36] demonstrated that Fkn and G glycoprotein inhibited >90% of 125 I Fkn polypeptide binding to 293-CX3CR1 cells at concentrations from 10 pM to 10 nM (FIG. 2). Scatchard analysis of the binding data revealed the $K_d$ for Fkn=5.8±1.4 nM and $K_d$ for G glycoprotein=2.1±1.6 nM.

CX3CR1 is a Receptor for RSV

The impact of G glycoprotein binding to CX3CR1 on the course of viral infection was also considered by examining RSV plaque reduction in Vero cells following treatment with heparin, Fkn, G glycoprotein, G glycoprotein peptides and anti-CX3CR1 (Table 3). CX3CR1 expression was detected on uninfected Vero cells (31-51% of cells) and RSV-infected Vero cells (60-85% of cells) by flow cytometry, and CX3CR1 mRNA was detected by RNAse protection analysis. The results of the infectivity assays (Table 3) were similar to those for the G glycoprotein binding inhibition studies (Table 2), in which G glycoprotein, Fkn, peptide RT33, anti-CX3CR1 antibody and heparin all inhibited plaque formation, but Δ+1, Δ−1, RT32 and RT34 glycoprotein peptides (Table 4), and normal rabbit sera had minimal to no effect. The increase over heparin-associated plaque reduction (66%) by the addition of G glycoprotein (98%), Fkn (97%), peptide RT33 (92%) and anti-CX3CR1 antibody (91%, (Table 3) suggest that RSV binds to CX3CR1 through the G glycoprotein. The peptides lacking the CX3C motif (RT32, RT34) or with changes in the CX3C motif (Δ+1 and Δ−1) (Table 4) did not increase heparin-associated plaque reduction (Table 3).

Figure 6:
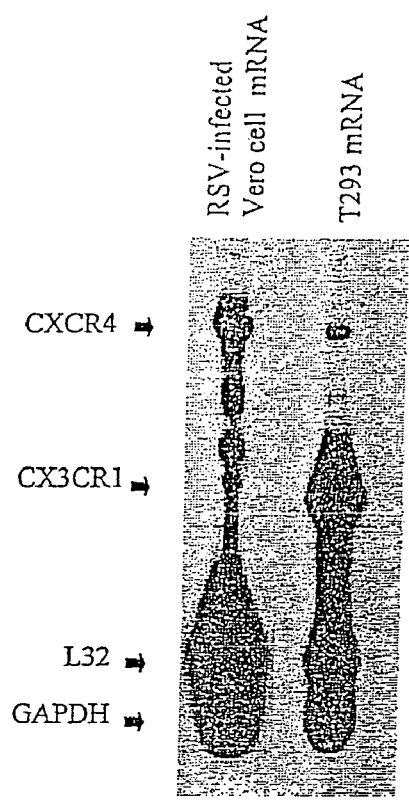
FIG. 6 is a computer-generated representation of an electrophoretic gel showing RNA Protection Analysis (RPA) of Vero cell mRNA from RSV/A2-infected (lane A) and CX3CR1-293 cells (lane B). mRNA was probed for the CXC-chemokine receptor-2 (CXCR2), CXC chemokine receptor-4 (CXCR4), CX3CR1 and housekeeping genes L32 and GAPDH.

These proteins had similar effects on plaque reduction using 10- and 100-fold higher inoculum of RSV. The specificity of G glycoprotein binding to CX3CR1 was further supported by the plaque reduction following treatment with anti-CX3CR1 antibody alone (38%). Inhibition by anti-CX3CR1 antibodies was comparable to inhibition by peptide RT33 alone (16%). Since RNA protection analysis showed that RSV infection increased CXCR4 mRNA expression (FIG. 6), plaque reduction by SDF-1α, a ligand for CXCR4 was performed, but no effect on RSV plaque formation was detected (Table 3).

G Glycoprotein Mediates Leukocyte Chemotaxis

Figure 3:
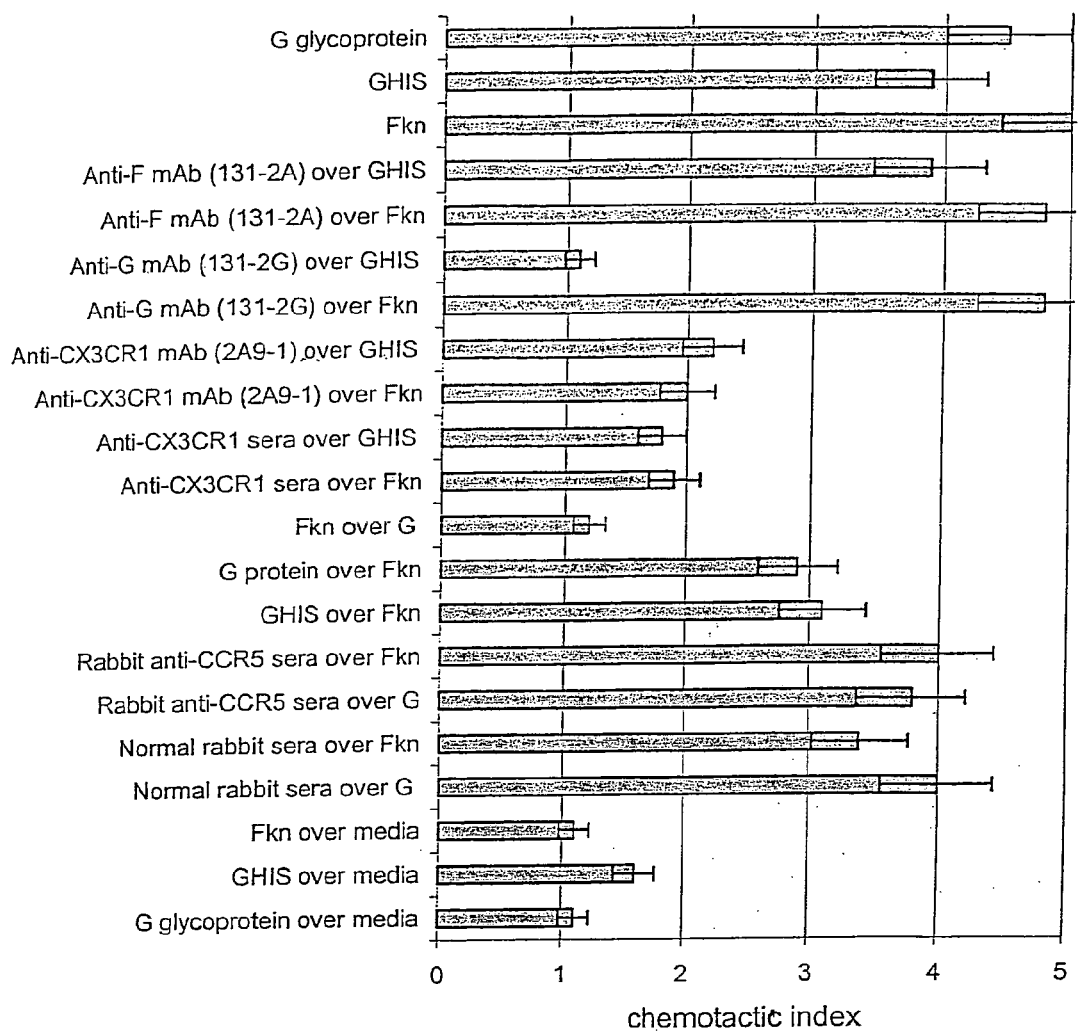
FIG. 3 shows the results of the chemotactic experiments. The chemotactic index was determined from the fold increase of murine spleen leukocyte cell migration toward the chemoattractant (e.g., Fkn or G glycoprotein) over the leukocyte migration toward media alone control, using modified Boyden chambers. Fkn, G glycoprotein, recombinant polyhistidine-tagged G glycoprotein (GHIS), anti-CX3CR1 monoclonal antibody (2A9-1), normal rabbit serum, rabbit anti-CX3CR1 serum, anti-G glycoprotein monoclonal antibody (131-2G) or anti-F glycoprotein monoclonal antibody (131-2A) were added to the upper chamber to examine antagonism of cell migration toward the chemoattractant in the lower chamber.

Since the G glycoprotein is a ligand for CX3CR1, whether it could act as a Fkn mimic to induce leukocyte chemotaxis of naive mouse leukocytes[39,40] and possibly alter Fkn-mediated leukocyte chemotaxis was tested. (FIG. 3). Both Fkn and G glycoprotein induced similar chemotactic indices (4.5-5.0) in a modified Boyden chamber. Anti-CX3CR1 antibodies inhibited leukocyte chemotaxis toward either the G glycoprotein or Fkn (chemotactic indices 1.8-2.2). Moreover, G glycoprotein inhibited leukocyte chemotaxis toward Fkn by approximately 37% (chemotactic index 3.2), whereas Fkn inhibited leukocyte chemotaxis toward G glycoprotein by approximately 75% (chemotactic index 1.2). In addition, anti-G glycoprotein (131-2G) inhibited leukocyte chemotaxis toward G glycoprotein (chemotactic index 1.1), but not toward Fkn (chemotactic index 4.8), and chemotaxis toward G glycoprotein or Fkn was not affected by anti-F glycoprotein (131-2A) treatment (chemotactic indices 3.9-4.8). The results of these inhibition studies suggest that G glycoprotein and Fkn induce chemotaxis through a similar mechanism.

Similar results were observed in chemotactic studies examining purified human peripheral blood mononuclear cells (PBMC) (Table 5). The total percent positive CX3CR1 expression for all cell types in the PBMC population prior to chemotaxis ranged 38-49%, however during incubation at 37° C., CX3CR1 expression declines and at 2 h post-incubation ranges between 21-38% expression, at 4 h post-incubation ranges between 11-26% expression and at 6 h post-incubation ranges between 8-30% expression. The decrease in CX3CR1 expression on PBMC during incubation likely reflects receptor endocytosis and recycling which is common among chemokine receptors[41]. At 6 h post-incubation in the Boyden chambers, the percent CX3CR1$^+$ leukocytes that migrated toward G glycoprotein or Fkn in the lower Boyden chamber was higher (25-30%) compared to the leukocytes remaining in the upper Boyden chamber (7-11%). Chemotaxis of leukocytes toward peptide RT33 in the lower Boyden chamber was modest (range 1.6-2.2). The substantial chemotactic indices for G glycoprotein and Fkn (3.0-3.7), the ability of G glycoprotein and Fkn to mutually reduce chemotaxis by the other, and higher CX3CR1 expression on leukocytes chemotactic toward 10 nM G glycoprotein or Fkn, suggest that both G glycoprotein and Fkn induce chemotaxis through similar mechanisms that involve CX3CR1. Addition of 1 μM peptide RT33 to the upper Boyden chambers reduced chemotaxis toward both G glycoprotein and Fkn, however the G glycoprotein peptides that lacked the CX3C motif (Table 4) did not reduce chemotaxis toward G or Fkn.

Figure 5A:
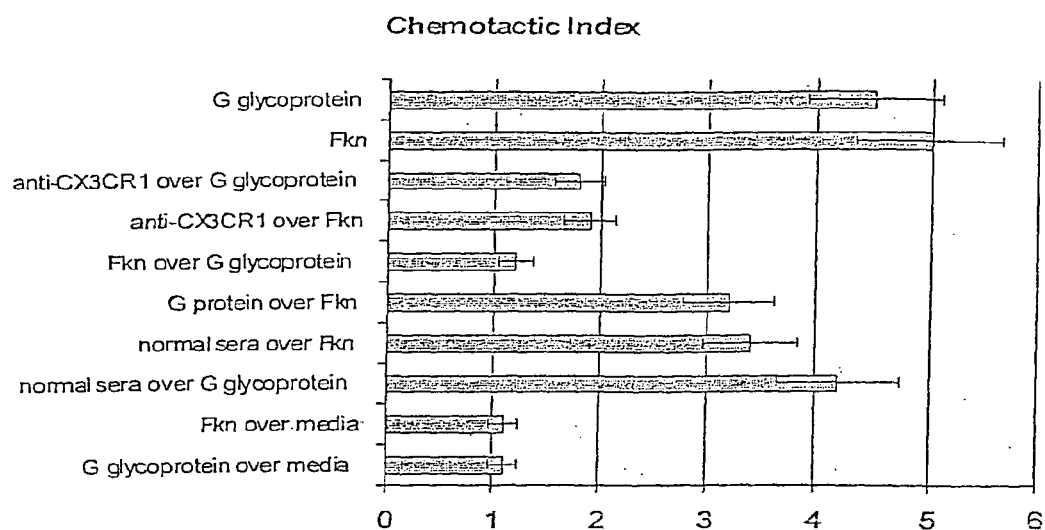
FIG. 5A is a bar graph showing leukocyte chemotaxis toward G glycoprotein or fractalkine (Fkn) in the presence or absence of anti-CX3CR1 antibody or normal rabbit sera. The chemotactic index determined from the fold increase of murine leukocyte migration toward the chemoattractant (e.g., Fkn or G glycoprotein) over the leukocyte migration toward the media alone control using modified Boyden chambers. Fkn, G glycoprotein, anti-CXCR1 antibody (10 µg) or normal rabbit sera (10 µg) was added to the upper chamber to examine antagonism of cell migration toward the chemoattractant in the lower chamber.
Figure 5B:
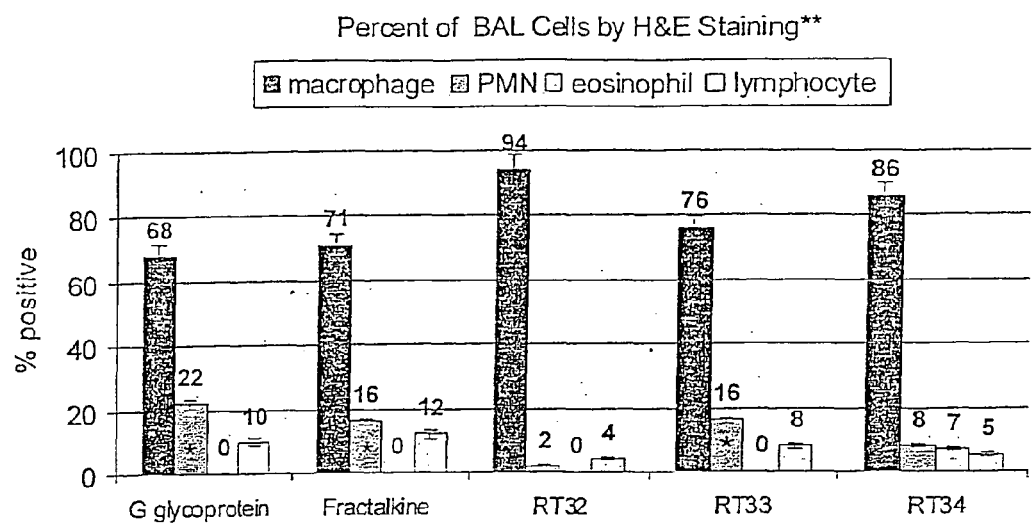
FIG. 5B is a bar graph showing cell trafficking to the lung of naïve BALB/c mice intranasally treated with G glycoprotein, fractalkine or G glycoprotein peptides RT32, RT33 or RT34. BAL cells were fixed and stained with H&E. Cell subsets were determined as a percentage of the total BAL cells counted from >200 cells/slide counting two slides for each experiment. The percent cell type represents the median±SE from three separate experiments. * indicates significant difference compared to tissue culture media alone ($p<0.05$). Naïve BALB/c mice were i.n. treated with 1 µM G glycoprotein or fractalkine or with 1 µM G glycoprotein peptides. The BAL was collected 2 days post-treatment for analysis.

Studies in naïve BALB/c mice show that G and Fkn also recruit leukocytes in vivo (FIG. 5B and Table 6). CX3CR1 is expressed on mouse and rat leukocytes, and by immunoprecipitation CX3CR1 was detected in naïve mouse splenocytes, a mouse monocytic cell line (LADMAC), as well as in a human epithelial cell line (HUT-292, data not shown). Naïve BALB/c mice were treated intranasally with G glycoprotein, Fkn or G glycoprotein peptides RT32, RT33 and RT34 (FIG. 2). The total number of BAL cells recovered at 48 hours post-treatment was increased with Fkn, G glycoprotein or peptide RT33 treatment. The mean BAL cell numbers (±SEM) recovered following treatment was 3.8 (±0.6)×10$^5$ cells/ml for Fkn, 4.6 (±1.1)×10$^5$ cells/ml for G glycoprotein and 3.5 (±0.3)×10$^5$ cells/ml for peptide RT33, compared to 2.2 (±0.5)×10$^5$ cells/ml for peptide RT32 or 2.8 (±0.2)×10$^5$ cells/ml for peptide RT34. Macrophages are the predominant cell type in the BAL irrespective of treatment, however treatment with G glycoprotein, Fkn and peptide RT33 resulted in recruitment of a higher percentage of PMNs and lymphocytes to the lung relative to treatment with peptides RT32 or RT34.

These data demonstrate that the G glycoprotein has structural similarities to Fkn and binds to cells in a manner similar to Fkn through CX3CR1 and GAG. The interaction between G glycoprotein and cells via CX3CR1 appears to have at least two important roles in the biology of RSV infection. First, interaction of the CX3C motif on the G glycoprotein with CX3CR1 on cells is capable of modulating the immune response as shown by the ability of G glycoprotein to induce migration of leukocytes in Boyden chamber experiments.

Second, G glycoprotein binding through CX3CR1 facilitates infection. The specificity of the G glycoprotein interaction with CXCR3 was analyzed through binding and binding inhibition assays with 293-CX3CR1 cells, and by two functional assays, RSV plaque reduction and leukocyte migration and migration inhibition assays. The results from these assays show increased G glycoprotein-binding correlates with increased expression of CX3CR1 on 293-CX3CR1 cells, and consistently indicated that G glycoprotein binds to CX3CR1 via the CX3C motif. The consistent results from three different G glycoprotein preparations examined, the use of anti-G glycoprotein monoclonal antibodies to detect or inhibit binding to 293-CX3CR1 cells, and leukocyte migration toward G glycoprotein demonstrate the specific role of G glycoprotein. The inhibition studies with reagents known to bind to CX3CR1 (Fkn, $^{125}$I-Fkn polypeptide, rabbit anti-CX3CR1 serum and an anti-CX3CR1 monoclonal antibody) support the specific role of CX3CR1 in this interaction. The inhibition studies with G glycoprotein peptides with or without the CX3C motif indicate that G glycoprotein interaction with CX3CR1 occurs, as expected, through the CX3C motif in the G glycoprotein. The data presented herein also indicate that much of the G glycoprotein and RSV binding to cells occurs via HBD-GAG interaction, and that the remaining binding to cells occurs mostly via G glycoprotein binding to CX3CR1.

The binding of RSV G glycoprotein to CX3CR1 on the surface of cells facilitates RSV infection of cells. These data show that CX3CR1 as well as GAG are receptors for RSV infection and that virus binding to CX3CR1 via the CX3C motif on the G glycoprotein explains some and possibly all of the non-GAG-associated binding to cells.

EXAMPLE II

Animals

Six-to-eight week old, specific-pathogen-free, female BALB/c (Jackson Laboratory, Bar Harbor, Me.) mice were used in all experiments. The mice were housed in microisolator cages and were fed sterilized water and food ad libitum. All studies were performed in accordance with the guidelines of the Institutional Animal Care and Use Committee.

Cell Lines

The African green monkey kidney epithelial cell line, Vero, was propagated in DME (GIBCO) containing 10% FBS (Hyclone), and cultured subconfluently in 75 cm2 flasks (Costar, Corning Inc., Corning, N.Y.) until use.

Virus and Infection

The A2 strain of RSV (RSV/A2) was used in all experiments and propagated in Vero cells as previously described (54, 55). Mice were anesthetized by i.p. administration of Avertin (2,2,2-tribromoethanol, 0.2 ml/g body weight, Sigma-Aldrich, St. Louis, Mo.), and i.n. challenged with 106 PFU of RSV in Dulbecco's PBS (GIBCO Laboratories, Grand Island, N.Y.). No fewer than three mice per treatment were examined per time point in three separate experiments.

Peptides

Peptide inhibition studies were examined using 5 G glycoprotein peptides: 1) RT33, a 12-mer G glycoprotein peptide encompassing the G glycoprotein CX3C motif (underlined, TCWAICKRIPNK (SEQ ID NO: 3)) in the amino acid sequence of the A2 strain of RSV (GENBANK, attachment protein locus 1912305, accession number M111486) (54), 2) RT34, a 12-mer G glycoprotein peptide C-terminal to the CX3C motif (NKKPGKKTTTKP) (SEQ ID NO: 4) (54), 3) EYp1, a 13-mer G glycoprotein peptide variant of RT33 containing a ALA substitution for ILE in the CX3C motif (TCAAACKRIPNKK) (SEQ ID NO: 5), 4) Δ-1, a 11-mer G glycoprotein peptide variant of RT33 with a deletion of ILE in the CX3C motif (TCWACKRIPNK) (SEQ ID NO: 16), (54), and 5) Δ+1, a 13-mer G glycoprotein peptide variant of RT33 with an ALA addition in the CX3C motif (TCWAIACKRIPNK) (SEQ ID NO: 17) (54). The peptides were synthesized using a simultaneous, multiple solid-phase peptide synthesis method on a peptide synthesizer (Perkin-Elmer Applied Biosystems, Berkeley, Calif.), and tested for homogeneity by reverse-phase liquid chromatography and capillary electrophoresis as previously described (56).

RSV Plague Reduction Assay

Different concentrations of the G glycoprotein peptides and/or 5 µg/ml heparin (Sigma) were diluted in Dulbecco's phosphate buffered saline (D-PBS; GIBCO) and added to Vero cell monolayers for 1 h at 37° C. Pre-treated Vero cells were infected with $10^6$ PFU of RSV/A2 diluted in serum-free DMEM (GIBCO) for 2 h at 37° C., after which DMEM (GIBCO) containing 10% FBS (Hyclone, Logan, Utah) was added, and the infected cells incubated at 37° C. for 3-4 days. Plaques were enumerated by immunostaining with monoclonal antibodies against the G and F glycoproteins (130-2G and 131-2A, respectively), as described (54,55).

In Vivo Peptide Treatment

On day −1, prior to RSV infection, mice were i.p. treated (0.1 ml/mouse) with 100 µM of G glycoprotein peptides RT33 (CWAIC) (SEQ ID NO: 12), RT34 (lacks the CX3C motif) or peptides with changes in the CX3C motif (Δ+1, Δ−1, EYp1). Control mice were treated with PBS containing a similar dilution of DMSO used to solubilize the peptides.

Cell Collection and Analysis

Mice were anesthetized with Avertin and exsanguinated by severing the right caudal artery. Bronchoalveolar leukocyte (BAL) cells were harvested by lung lavage with PBS containing 1% bovine serum albumin (BSA, Sigma). The procedure used for extracellular staining of BAL cells was modified for microculture staining as described (55,57). Briefly, BAL cells were washed in Dulbecco's PBS (GIBCO) containing 1% bovine serum albumin (Sigma), blocked with 10% normal mouse sera diluted in PBS containing 1% bovine serum albumin, and then stained (4° C., 30 min) with an appropriate dilution of FITC-conjugated or PE-conjugated anti-CD3ε (145-2C11), anti-CD45R/B220 (RA3-6B2), anti-CD8 (Ly-2), anti-neutrophil (PMN) (RB6-8C5), anti-CD11b (M1/70) and isotype antibody controls (all from Pharmingen, San Diego, Calif.).

Intracellular cytokine staining was modified for microculture staining as described (55, 57). Briefly, BAL cells were incubated in PBS containing Golgi Stop (Pharmingen) for 3 h at 37° C. to allow for accumulation of intracellular cytokines. The cells were washed in PBS containing 1% bovine serum albumin, blocked with 10% normal mouse sera diluted in PBS containing 1% bovine serum albumin, and stained (4° C., 30 min) with an appropriate dilution of anti-CD3 antibody, fixed and permeabilized in Cytofix/Cytoperm (Pharmingen). The cells were washed in Cytofix/Cytoperm buffer and stained (4° C., 30 min) with appropriate dilutions of anti-IL-2 (JES6-5H4), anti-IL-4 (BVD4-1D11), anti-IL-5 (TRFK5), IL-10 (JES3-16E3), anti-IFNγ (XMG1.2), or anti-TNFα (MP6-XT22) antibodies (Pharmingen) diluted in Cytofix/Cytoperm. Extra- and intracellular staining was analyzed by flow cytometry using a FACScan and Cell Quest software (Becton Dickinson, San Diego, Calif.). Total cytokine expression by CD3+ T cells was determined from the percent cytokine expression of CD3+ T cells and total number of cells recovered. The total number of CD3+ BAL cells expressing a particular cytokine was determined by multiplying the total number of BAL cells by the percent CD3+ cells expressing that particular cytokine.

Virus Titers

Virus titers in the lungs of RSV-infected mice were determined as previously described (55, 58). Briefly, lungs were aseptically removed from 3-5 mice per group at days 3, 5, 7 and 9 pi, and stored at −70° C. until assay. Identical weights (0.1 g) of individual lung samples were homogenized in 1 ml of Dulbecco's PBS (GIBCO), and ten-fold serial dilutions of the lung homogenates were added to 80-90% confluent Vero cell monolayers. Following adsorption (2 h, 37° C.), cell monolayers were overlaid with DMEM (GIBCO) containing 10% FBS (Hyclone, Logan, Utah), and incubated at 37° C. for 3-4 days in static conditions. Plaques were enumerated by immunostaining with monoclonal antibodies against the G and F glycoproteins (130-2G and 131-2A, respectively), as previously described (55, 58).

Statistical Analysis

Statistical significance was determined using a Student's t test where $p<0.05$ was considered statistically significant.

RSV Plaque Reduction by Small Molecule Peptide Inhibitors

Figure 7:
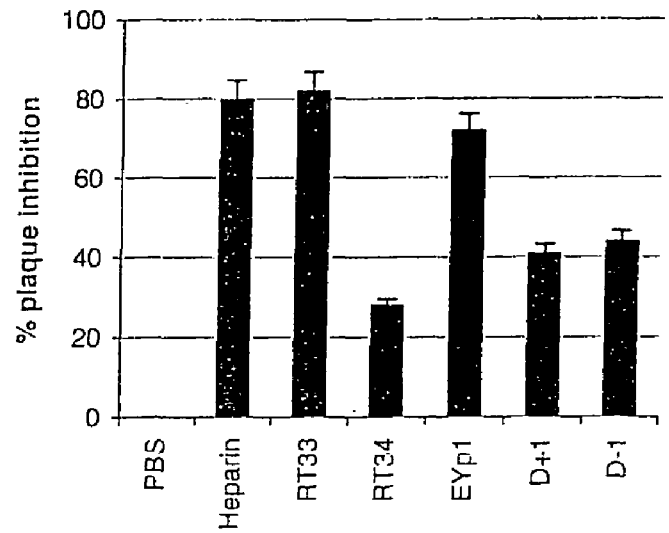
FIG. 7 shows RSV plaque reduction by small molecule peptide inhibitors. Vero cells were treated with PBS, RT33, RT34, Δ+1, Δ−1 and EYp1 peptides (100 µm) in the presence (B) or absence of heparin (A) (5 µg/ml). Percentage inhibition was determined by dividing the mean plaque forming units (PFU) of treated Vero cells by the mean PFU of PBS-treated Vero cells.
Figure 7:
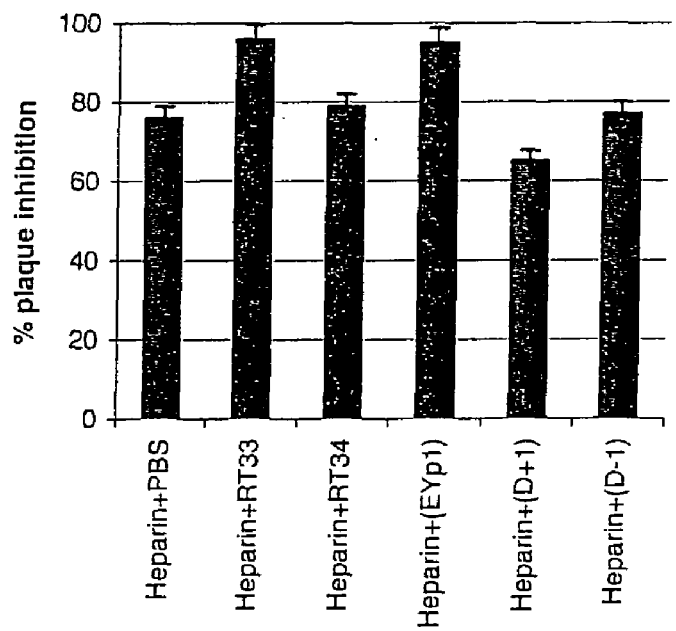

Small molecule inhibition of RSV infection of Vero cells was examined using peptides RT33, RT34, EYp1, Δ+1, Δ−1, or PBS in the presence or absence of 5 μg/ml heparin (FIG. 7). Treatment of Vero cells with peptides containing a CX3C motif, i.e. RT33 (CWAIC) (SEQ ID NO: 12) or EYp1 (CAAAC) (SEQ ID NO: 15), in the absence of heparin, inhibited between 72-82% of plaque formation, while treatment with heparin alone inhibited 80% of plaque formation (FIG. 7A). Peptides with modifications to the CX3C motif, i.e. Δ+1 or Δ−1, or absent of a CX3C motif, i.e. RT34, reduced plaque formation between 28-44% in the absence of heparin. Addition of peptides RT33 or EYp1 to heparin improved plaque reduction (95-96% inhibition) from heparin treatment alone (80%), while addition of Δ+1, Δ−1, or RT34 peptides to heparin had no effect above heparin treatment alone (FIG. 7B). CX3CR1 has been shown to be expressed on uninfected and RSV-infected Vero cells (54), and these results are consistent with a previous observation from this laboratory that heparin or RT33 treatment alone is sufficient to inhibit the majority of plaque formation.

Figure 8:
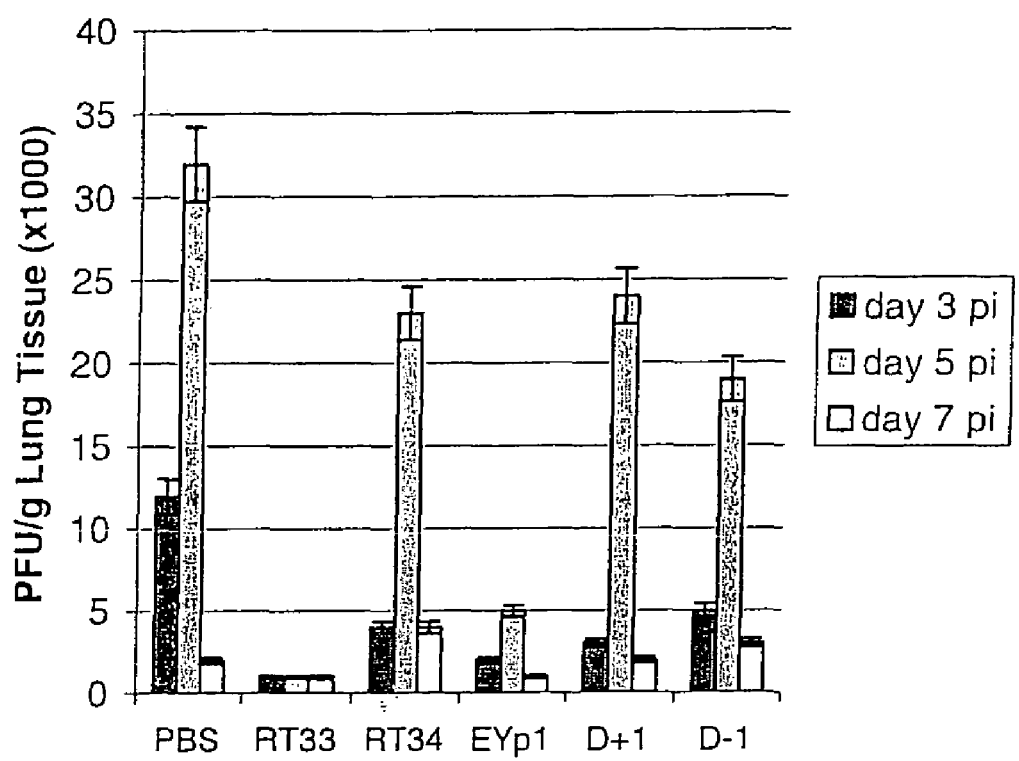
FIG. 8 shows RSV lung titers following in vivo peptide treatment. The lungs of peptide-treated and control mice were harvested at days 3, 5, 7, and 14 post-RSV infection. The results are expressed as PFU/g±SEM.

Treatment of Mice with Small Molecule Peptide Inhibitors and RSV Titers in the Lung To address the effectiveness of small molecule peptide inhibitors in vivo, mice were treated with peptides RT33, RT34, EYp1, Δ+1, Δ−1, or PBS a day prior to RSV challenge, and the viral titers in the lung determined at days 3, 5, and 7 pi (FIG. 8). High titers of virus were detected in lungs of mice treated with PBS or peptides lacking the CX3C motif, i.e. RT34, Δ+1, or Δ−1 at day 5 pi ($1.8$-$3.3 \times 10^4$ pfu/g lung tissue), however mice treated with peptides containing a CX3C motif, i.e. RT33 or EYp1, had dramatically lower virus titers (0.1-$0.4 \times 10^4$ pfu/g lung tissue). By day 14 pi, no virus was detected in lungs of any treated mice. Interestingly, peptide treatment was associated with lower virus titers at day 3 pi, compared to PBS-treated mice, suggesting that treatment may augment aspects of innate immunity.

Small Molecule Peptide Inhibitors and Pulmonary Cell Infiltration

Figure 9:
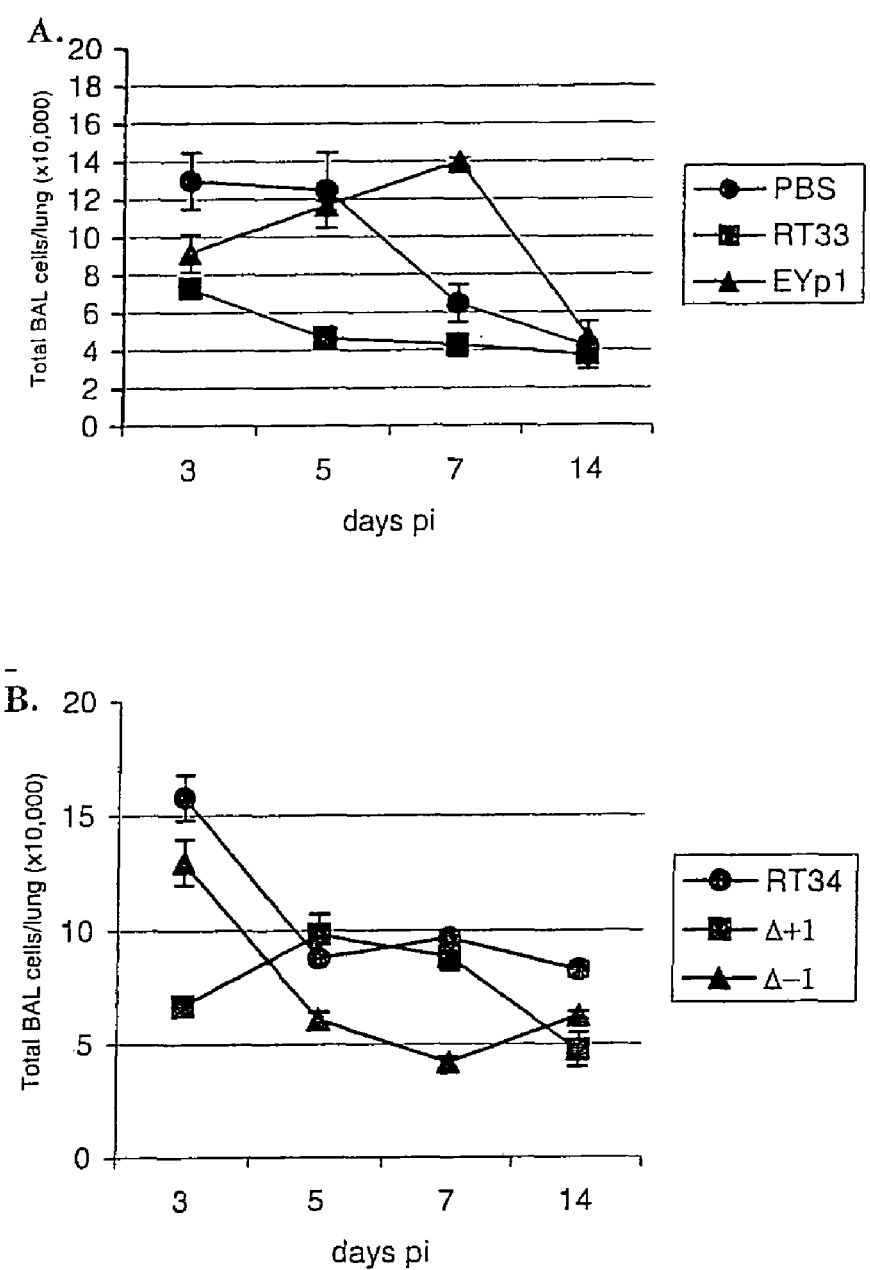
FIG. 9 shows total BAL cell infiltration following in vivo peptide treatment. Total pulmonary leukocyte trafficking following treatment of mice with peptides containing a CX3C motif (RT33 and EYp1) (A) or peptides without a CX3C motif (RT34, Δ+1, Δ−1)(B).

The total number of bronchoalveolar leukocytes (BAL) recovered from peptide- or PBS-treated mice infected with RSV was determined at days 3, 5, 7 and 14 pi (FIG. 9). The influx of BAL numbers associated with peptide treatment did not appear to correlate with virus clearance (FIG. 8). Mice treated with peptides containing a CX3C motif, i.e. RT33 or EYp1, had reduced BAL numbers at day 3 pi (FIG. 9A), compared to mice treated with peptides RT34 or Δ−1 (FIG. 9B) or PBS. An exception was treatment with peptide Δ+1, which was associated with a reduced BAL infiltrate. BAL numbers in mice treated with peptide RT33 declined from day 3 to day 14 pi, however BAL numbers increased over this time period in mice treated with peptides EYp1 or Δ+1, before declining at day 14 pi. The increase in BAL numbers observed between days 5 and 7 pi in EYp1 and Δ+1 peptide-treated mice suggests that these peptides may be immune stimulatory, particularly for peptide EYp1, since very low viral lung titers were detected in mice treated with this peptide (FIG. 8). By day 14 pi, BAL numbers were low in all peptide- and PBS-treated mice compared to day 3 pi.

Figure 10:
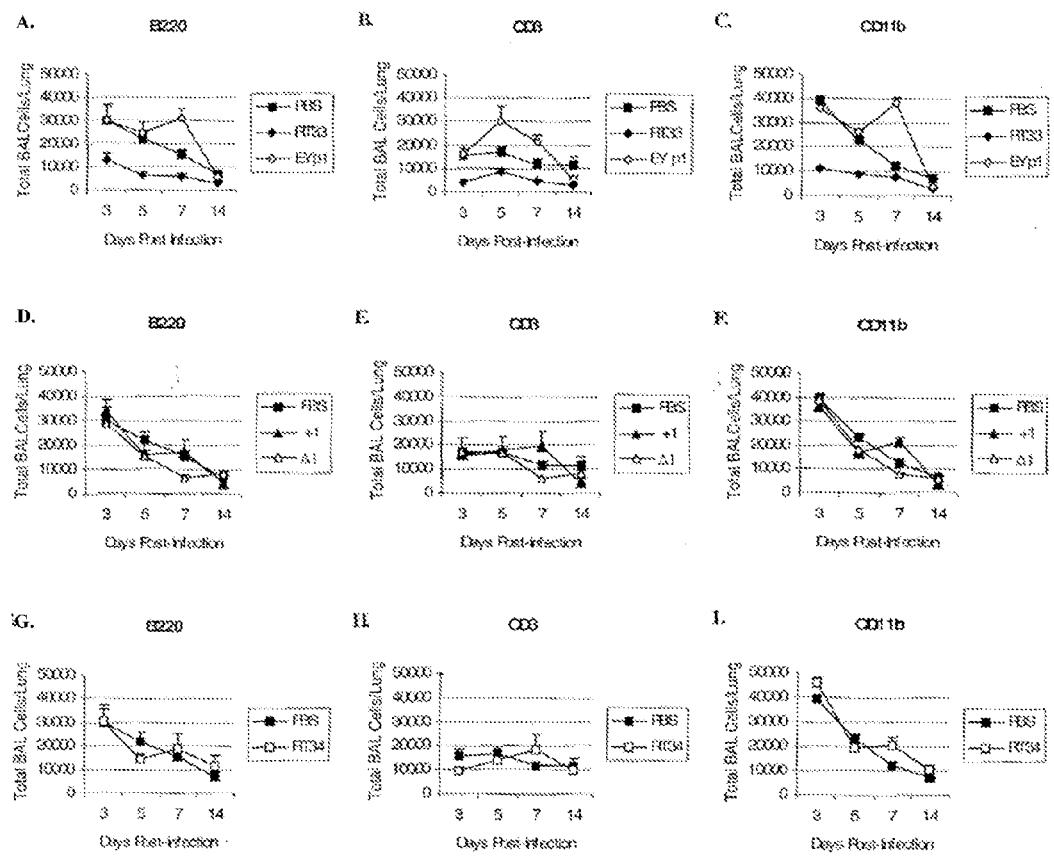
FIG. 10 shows BAL cell types in RSV-infected mice following in vivo peptide treatment. Flow cytometry results following treatment (d−1) of mice with PBS, RT33, RT34, Δ+1, Δ−1 and EYp1 peptides (100 µm). BAL cells were stained with antibodies against $B220^+$ (A, D, G), $CD3^+$ (B, E, H) and $CD11b^+$ (C, F, I) cells. Data is expressed as the total BAL cells/lung±SEM at days 3, 5, 7 and 14 post-infection. A representative experiment from 3 independent experiments is shown.
Figure 11:
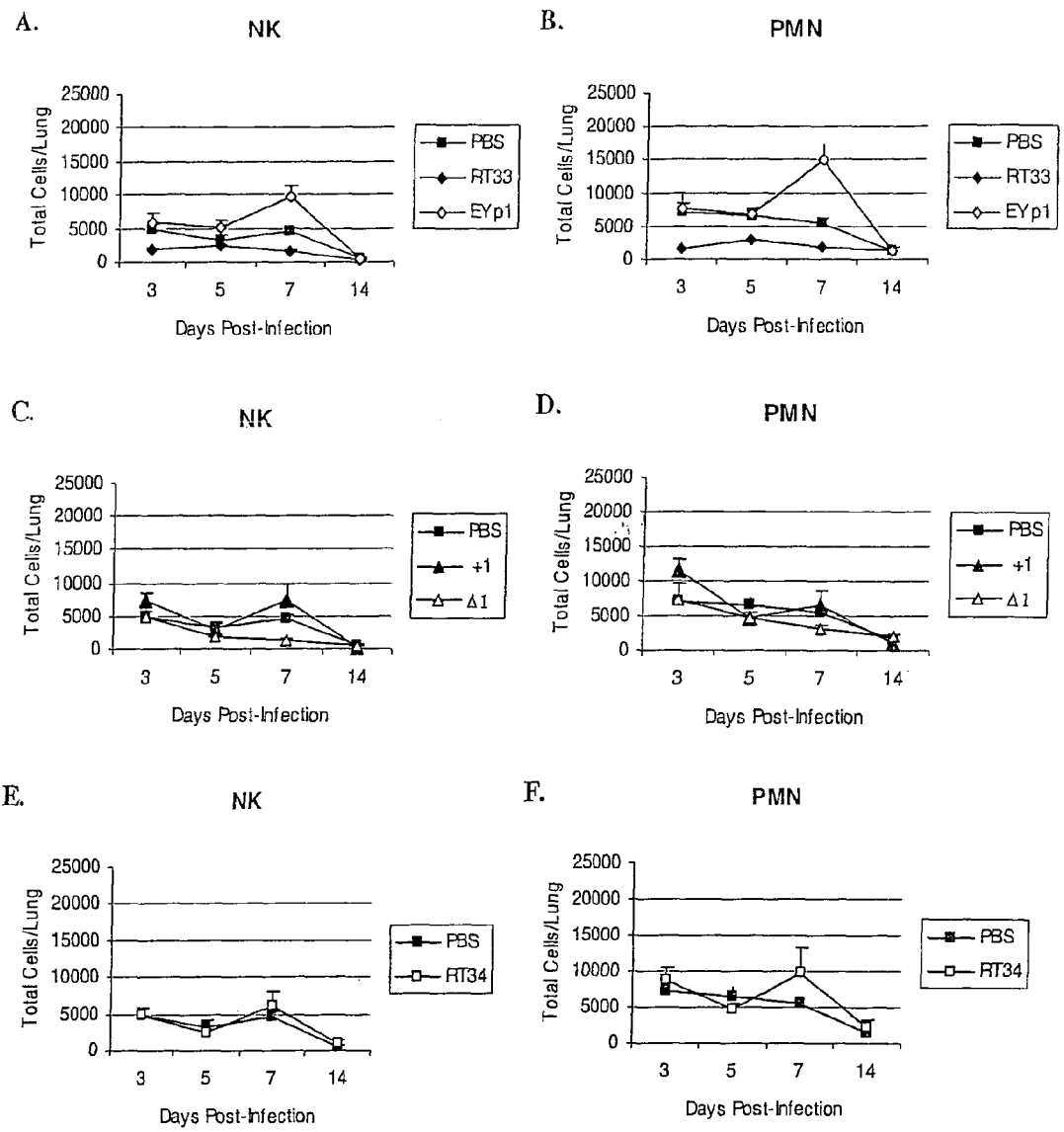
FIG. 11 shows BAL cell types in RSV-infected mice following in vivo peptide treatment. Flow cytometry results following treatment (d−1) of mice with PBS, RT33, RT34, Δ+1, Δ−1 and EYp1 peptides (100 µm). BAL cells were stained with antibodies against NK ($DX5^+$) (A, C, E) and PMN ($RB6-8C5^+$) cells (B, D, F). Data is expressed as the total BAL cells/lung±SEM at days 3, 5, 7 and 14 post-infection. A representative experiment from 3 independent experiments is shown.

BAL Cell Types in RSV-Infected Mice Treated with Small Molecule Peptide Inhibitors To determine the effect of peptide treatment on BAL cell types in the lungs of RSV-infected mice, the total number of $B220^+$, $CD3^+$, and $CD11b^+$ cells (FIG. 10) or NK or PMN cells (FIG. 11) was determined at days 3, 5, 7 and 14 pi. At day 3 pi, $B220^+$ (FIG. 10A) and $CD11b^+$ (FIG. 10C) cells were the predominate cell types in peptide- or PBS-treated mice, compared to CD3+ (T cell), DX5+(NK cell) and RB6-8C5+ (PMN) cells. Mice treated with peptide RT33 had reduced numbers of BAL cell types compared to mice treated with RT34, EYp1, Δ+1 or Δ−1 peptides or PBS. The increase in BAL numbers at days 3-7 pi in mice treated with peptide EYp1 (FIG. 9), was associated with increased numbers of CD3+ cells on days 5 and 7 pi (FIG. 10), and increased numbers of $B220^+$, $CD11b^+$ (FIG. 4), PMN and NK cells on day 7 pi (FIG. 11). The total number of BAL cell types in mice treated with Δ+1, Δ−1 or RT34 peptides was similar to PBS-treated mice, peaking at day 3 pi and declining at a similar rate at day 14 pi (FIGS. 10 and 11).

Small Molecule Peptide Inhibitors and Intracellular Cytokine Expression by BAL Cells Th1- and Th2-type cytokine expression by BAL cells was determined in RSV-infected mice treated with small molecule peptide inhibitors or PBS at days 3, 5, 7, and 14 pi (Table 7). Th1 or Th2 intracellular cytokine expression was highest at day 3 pi in mice treated with any peptide, however at day 5 pi, Th1 and Th2 cytokine expression was significantly decreased in the peptide-treated mice compared to PBS-treated mice. At day 3 pi, $CD3^+$ T lymphocytes from mice treated with peptides RT33, EYp1 or Δ+1, expressed significantly lower Th1-type (IL-2, IFNγ and TNFα) and Th2-type (IL-4, IL-5 and IL-6) cytokines, compared to mice treated with PBS or peptides RT34 or Δ−1. An exception was IL-5 expression in mice treated with peptide RT34. At day 5 pi, the level of Th1- and Th2-type cytokine expression was lowest in mice treated with peptide RT33. Between days 7 and 14 pi, Th1- or Th2-type cytokine was low for all peptide treatments coinciding with virus clearance at day 7 pi (FIG. 8). The inhibition of RSV infection (FIG. 8), and reduction of Th1- and Th2-type cytokine expression (Table 7) observed in mice treated with RT33 or EYp1 peptides, suggests that these small molecule inhibitors may be useful for ameliorating RSV infection and cytokine-associated disease pathogenesis.

In this study, the ability of small molecule peptide inhibitors of the chemokine receptor, CX3CR1, to inhibit RSV infection in vitro and in vivo was examined. Peptide inhibitors containing a CX3C motif (RT33 and EYp1) dramatically inhibited RSV infection of Vero cells and RSV infection in BALB/c mice, compared to mice treated with peptides that lack a CX3C motif (RT34, Δ+1, Δ−1). These results suggest that RSV-CX3CR1 interaction is important during infection, and support the finding that the CX3C motif in the G glycoprotein interacts with CX3CR1 to facilitate RSV infection. In addition, mice treated with peptides RT33 and EYp1, exhibited reduced Th1/Th2- and pro-inflammatory cytokine expression, suggesting that peptide inhibitors containing a CX3C motif may also alter cytokine-based inflammation.

Treatment with peptides EYp1 or RT33 resulted in similar inhibition of RSV infection in Vero cells and in mice; however, the pulmonary cell infiltrate in EYp1 treated mice increased from days 3-7 pi, while BAL cell numbers decreased over the same time period in RT33-treated mice. Low levels of infectious virus were recovered from the lungs of EYp1- and RT33-treated mice, suggesting that the increase in BAL cell numbers in EYp1-treated mice was not associated with virus replication. It is possible that the mechanisms linked to peptide inhibition of RSV infection, and the induction of chemokines by cell types expressing CX3CR1, is distinct. Peptide EYp1 has a neutral CX3C motif (CAAAC) (SEQ ID NO: 15) compared to peptide RT33 (CWAIC) (SEQ ID NO: 12). Replacement of TRP-ALA-ILE in peptide RT33, with ALA-ALA-ALA in peptide EYp1, may enhance the avidity of CX3CR1 interaction, and trigger the induction of chemokines or other factors that induce pulmonary leukocyte chemotaxis.

Bioavailability may also be an important factor that may impact the efficacy of small molecule peptide inhibitors of virus infection. Many peptides used as pharmaceutical agents need carboxy amidation for full activity or prolonged bioavailability, and topographical modifications to conformationally-restricted peptides can significantly modulate potency, binding capacity, and enzymatic stability resulting in a change of bioavailability. For example, N-terminal modifications to somatostatin octapeptide analogs have been shown to enhance both potency and selectivity for its receptor, and improve the duration of action and bioavailability in the rat. Thus, the differences in BAL cell infiltration observed between peptide EYp1 and RT33, may relate to differences in the bioavailability of the peptides.

For greater than four decades, there has been a need for effective therapeutic or prophylactic anti-viral agents to combat RSV infection. Limited progress has been made because of an incomplete understanding of the mechanisms associated with RSV infection, the immune response to infection, and disease pathogenesis. This discovery of RSV G glycoprotein CX3C interaction with the chemokine receptor, CX3CR1 opens a new avenue for investigating some of the mechanisms that may contribute to RSV infection, immunity, and disease pathogenesis. The results from this study show that small molecule peptide inhibitors containing a CX3C motif can be useful for ameliorating RSV infection, and can be useful for reducing HIV interaction with CX3CR1.

Throughout this application, various publications are referenced. The disclosures of these publications in their entireties are hereby incorporated by reference into this application in order to more fully describe the state of the art to which this invention pertains.

REFERENCES

1. Chanock, R. M., Parrott, R. H., Connors, M., Collins, P. L. & Murphy, B. R. Serious respiratory tract disease caused by respiratory syncytial virus: prospects for improved therapy and effective immunization. *Pediatrics* 90, 137-143 (1992).
2. Fixler, D. E. Respiratory syncytial virus infection in children with congenital heart disease: a review. *Ped. Cardiol.* 17, 163-168 (1996).
3. McIntosh, K. & Fishaut, J. M. Immunopathologic mechanisms in lower respiratory tract disease of infants due to respiratory syncytial virus. *Prog, Med. Viro.* 26, 94-118 (1980).
4. Hall, C. B. Respiratory syncytial virus: A continuing culprit and conundrum. *J. Ped.* 135, 2-7 (1999).
5. Chin, J., Magoffin, R. L., Shearer, L. A., Schieble, J. H. & Lennette, E. H. Field evaluation of a respiratory syncytial virus vaccine and a trivalent parainfluenza virus vaccine in a pediatric population. *Am. J. Epidemiol.* 89, 449-463 (1969).
6. Weibel, R. E., Stokes, J., Jr., Leagus, M. B., Mascoli, C. C. & Hilleman, M. R. Respiratory virus vaccines. V. Field evaluation for efficacy of heptavalent vaccine. *A.m. Rev. Resp. Dis.* 94, 362-379 (1966).
7. Connors, M., Collins, P. L., Firestone, C.-Y. and Murphy, B. R. Respiratory syncytial virus (RSV) F, G, M2 (22K), and N proteins each induce resistance to RSV challenge, but resistance induced by M2 and N proteins is relatively short-lived. *J. Virol.* 65:1634-1637 (1991).
8. Stott, E. J., et al. Immune and histopathological responses in animals vaccinated with recombinant vaccinia viruses that express individual genes of human respiratory syncytial virus. *J. Virol.* 61, 3855-3861 (1987).
9. Groothuis, J. R., King, S. J., Hogerman, D. A., Paradiso, P. R. & Simoes, E. A. Safety and immunogenicity of a purified F protein respiratory syncytial virus (PFP-2) vaccine in seropositive children with bronchopulmonary dysplasia. *J. Infect. Dis.* 177, 467-469 (1998).
10. Olmsted, R. A., et al. Expression of the F glycoprotein of respiratory syncytial virus by a recombinant vaccinia virus: comparison of the individual contributions of the F and G glycoproteins to host immunity. *Proc. Nat. Acad. Sci., USA* 83, 7462-7466 (1986).
11. Bright, H., Turnbull, T., Toms, G. L. & Scott, R. Comparison of the T helper cell response induced by respiratory syncytial virus and its fusion protein in BALB/c mice. *Vaccine* 13, 915-922 (1995).
12. Graham, B. S, et al. Priming immunization determines T helper cytokine mRNA expression patterns in lungs of mice challenged with respiratory syncytial virus. *J. Immunol.* 151, 2032-2040 (1993).
13. Srikiatkhachorn, A. & Braciale, T. J. Virus-specific memory and effector T lymphocytes exhibit different cytokine responses to antigens during experimental murine respiratory syncytial virus infection. *J. Virol.* 71, 678-685 (1997).
14. Kurt-Jones, et al. Pattern recognition receptors TLR4 and CD 14 mediate response to respiratory syncytial virus. *Nature Immunol.* 1, 398-401 (2000).
15. Openshaw, P. J. Immunity and immunopathology to respiratory syncytial virus. The mouse model. *Amer. J. Respir. &Crit. Care Med.* 152, S59-62 (1995).
16. Johnson, T. R., et al. Priming with secreted glycoprotein G of respiratory syncytial virus (RSV) augments interleukin-5 production and tissue eosinophilia after RSV challenge. *J. Virol.* 72, 2871-2880 (1998).
17. Hancock, G. E., et al. Generation of atypical pulmonary inflammatory responses in BALB/c mice after immunization with the native attachment (G) glycoprotein of respiratory syncytial virus. *J. Virol.* 70, 7783-7791 (1996).
18. Sparer, T. E., et al. Eliminating a region of respiratory syncytial virus attachment protein allows induction of protective immunity without vaccine-enhanced lung eosinophilia. *J. Exp. Med.* 187, 1921-1926 (1998).
19. Tebbey, P., Hagen, M. & Hancock, G. Atypical pulmonary eosinophilia is mediated by a specific amino acid sequence of the attachment (G) protein of respiratory syncytial virus. *J. Exp. Med.* 188, 1967-1972 (1998).

20. Tripp, R. A. et al. Respiratory syncytial virus (RSV) G and/or SH proteins alter Th1 cytokines, natural killer cells and neutrophils responding to pulmonary infection in BALB/c mice. *J. Virol.* 73, 7099-7107 (1999).

21. Tripp, R. A., Jones, L. & Anderson, L. J. Respiratory syncytial virus G and/or SH glycoproteins modify CC and CXC chemokine mRNA expression in the BALB/c mouse. *J. Virol.* 74, 6227-6229 (2000).

22. Feldman, S. A., Hendry, R. M. & Beeler, J. A. Identification of a linear heparin binding domain for human respiratory syncytial virus attachment glycoprotein G. *J. Virol.* 73, 6610-6617 (1999).

23. Witt, D. P. & Lander, A. D. Differential binding of chemokines to glycosaminoglycan subpopulations. *Curr. Biol.* 4, 394-400 (1994).

24. Driscoll, K. E. Macrophage inflammatory proteins: biology and role in pulmonary inflammation. *Exp. Lung Res.* 20, 473-490 (1994).

25. Lalani, A. S., et al. The purified myxoma virus gamma interferon receptor homolog M-T7 interacts with the heparin-binding domains of chemokines. *J. Virol.* 71, 4356-4363 (1997).

26. Koopmann, W., Ediriwickrema, C. & Krangel, M. S. Structure and function of the glycosaminoglycan binding site of chemokine macrophage-inflammatory protein-1 beta. *J. Immunol.* 163, 2120-2127 (1999).

27. Johnson, P. R., Spriggs, M. K., Olmsted, R. A. & Collins, P. L. The G glycoprotein of human respiratory syncytial viruses of subgroups A and B: extensive sequence divergence between antigenically related proteins. *Proc. Nat. Acad. Sci., USA* 84, 5625-5629 (1987).

28. Melero, J. A., Garcia-Barreno, B., Martinez, I., Pringle, C. R., & Cane, P. A. Antigenic structure, evolution and immunobiology of human respiratory syncytial virus attachment (G) protein. *J. Gen. Virol.* 75, 2411-2418 (1997).

29. McDermott, D. H., & Murphy, P. M. Chemokines and their receptors in infectious disease. *Springer Sem. Immunopathol.* 22, 393-415 (2000).

30. Loetscher, P., Moser, B. & Baggiolini, M. Chemokines and their receptors in lymphocyte trafficking and HIV infection. *Adv. Immunol.* 74, 127-180 (2000).

31. Beisser, P. S., et al. Human cytomegalovirus chemokine receptor gene US28 is transcribed in latently infected THP-1 monocytes. *J. Virol.* 75, 5949-5957.

32. Endres, M. J., Garlisi, C. G., Xiao, H., Shan, L. & Hendrick, J. A. The Kaposi's sarcoma-related herpesvirus (KHSV)-encoded chemokine vMIP-1 is a specific agonist for the CC chemokine receptor (CCR)8. *J. Exp. Med.* 189, 1993-8 (1999).

33. Combadiere, C., et al. Identification of CX3CR1. A chemotactic receptor for the human CX3C chemokine fractalkine and a fusion coreceptor for HIV-1. *J. Biol. Chem.* 273, 23799-23804 (1998).

34. Anderson, L. J., et al. Antigenic characterization of respiratory syncytial virus strains with monoclonal antibodies. *J. Infect. Dis.* 15, 626-633 (1985).

35. Sullender, W. Antigenic analysis of chimeric and truncated RSV G glycoproteins of respiratory syncytial virus. *Virol.* 209, 70-79 (1995).

36. Combadiere, C., Gao, J., Tiffany, H. L. & Murphy, P. M. Gene cloning, RNA distribution, and functional expression of mCX3CR1, a mouse chemotactic receptor for the CX3C chemokine fractalkine. *Bio. & Biophys. Res. Comm.* 253, 728-732 (1998).

37. Bourgeois, C., Bour, J. B., Lidholt, K., Gauthray, C. & Pothier, P. Heparin-like structures on respiratory syncytial virus are involved in its infectivity in vitro. *J. Virol.* 72, 7221-7227 (1998).

38. Hallak, L. K., Collins, P. L., Knudson, W. & Peeples, M. E. Iduronic acid-containing glycosaminoglycans on target cells are required for efficient respiratory syncytial virus infection. *Virol.* 271, 264-275 (2000).

39. Schall, T. Fractalkine—a strange attractor in the chemokine landscape. *Immunol. Today* 18, 147-152 (1997).

40. Fong, A. M. et al. Fractalkine and CX3CR1 mediate a novel mechanism of leukocyte capture, firm adhesion, and activation under physiologic flow. *J. Exp. Med.* 188, 1413-1419 (1998).

41. Pelchen-Matthews, A., et al. Chemokine receptor trafficking and viral replication. *Immuno.l Rev.* 168, 33-49 (1999).

42. Karron, R. A. et al. Respiratory syncytial virus (RSV) SH and RSV G glycoproteins are not essential for viral replication in vitro: clinical evaluation and molecular characterization of a cold-passaged, attenuated RSV subgroup B mutant. *Proc. Nat. Acad. Sci., USA* 94, 13961-1396 (1997).

43. Feldman, S. A., Audet, S. & Beeler, J. A. The fusion glycoprotein of human respiratory syncytial virus facilitates virus attachment and infectivity via an interaction with cellular heparin sulfate. *J. Virol.* 74, 6442-6447 (2000)

44. Roder, C., Krusat, T., Reimers, K., & Werchu, H. Purification of respiratory syncytial virus F and RSV G glycoproteins. *J. Chromat.* 737:97-106 (2000).

45. Tripp, R. A., Moore, D., Winter, J. & Anderson, L. J. Respiratory syncytial virus infection and G and/or SH protein expression contribute to substance P, which mediates inflammation and enhanced pulmonary disease in BALB/c mice *J. Virol.* 74, 1614-1622 (2000).

46. Boyden, S. The chemotactic effect of mixtures of antibody and antigen on polymorphonuclear leukocytes. *J. Exp. Med.* 115, 453-466 (1962).

47. *Remington's Pharmaceutical Sciences* (Martin, E. W., ed., latest edition), Mack Publishing Co., Easton, Pa.

48. Michieli, P., Li, W., Lorenzi, M. V., Miki, T., Zakut, R., Givol, D., and Pierce, J. H. *Oncogene* 12, 775-784, 1996.

49. Sambrook et al., *Molecular Cloning: A Laboratory Manual*, 2nd Ed., Cold Spring Harbor Laboratory, Cold Spring Harbor, N.Y., 1989.

50 U.S. Pat. No. 4,704,36

51. Brake et al., 1984. Alpha-factor-directed synthesis and secretion of mature foreign proteins in *Saccharomyces cerevisiae*. *PNAS* 82:4642-4646.

52. Kearney et al., *J. Immunol.* 123:1548-1558 (1979).

53. Jones et al., *Nature* 321:522-525 (1986) or Tempest et al. *Biotechnology* 9:266-273 (1991).

54. Tripp, R. A., L. P. Jones, L. M. Haynes, H. Zheng, P. M. Murphy, and L. J. Anderson. 2001. CX3C chemokine mimicry by respiratory syncytial virus G glycoprotein. *Nat Immunol* 2:732-8.

55. Tripp, R. A., D. Moore, L. Jones, W. Sullender, J. Winter, and L. J. Anderson. 1999. Respiratory syncytial virus G and/or SH protein alters Th1 cytokines, natural killer cells, and neutrophils responding to pulmonary infection in BALB/c mice. *J Virol* 73:7099-107.

56. Crowe, J. E., Jr., B. R. Murphy, R. M. Chanock, R. A. Williamson, C. F. Barbas, 3rd, and D. R. Burton. 1994.

Recombinant human respiratory syncytial virus (RSV) monoclonal antibody Fab is effective therapeutically when introduced directly into the lungs of RSV-infected mice. *Proc Natl Acad Sci USA* 91:1386-90.

57. Tripp, R. A., D. Moore, and L. J. Anderson. 2000. TH(1)- and TH(2)-TYPE cytokine expression by activated t lymphocytes from the lung and spleen during the inflammatory response to respiratory syncytial virus. *Cytokine* 12:801-7.

58. Tripp, R. A., and L. J. Anderson. 1998. Cytotoxic T-lymphocyte precursor frequencies in BALB/c mice after acute respiratory syncytial virus (RSV) infection or immunization with a formalin-inactivated RSV vaccine. *J Virol* 72:8971-5.

TABLE 1

G glycoprotein and Fkn binding to 293 and 293-CX3CR1 cells.

| | Fkn-Maximum Binding (%)[#] | | | |
|---|---|---|---|---|
| | 10 nM | 1 nM | 100 pM | 10 pM |
| G glycoprotein | 88 | 87 | 80 | 40 |
| Fkn | 98 | 99 | 98 | 46 |

The percent Fkn-maximum binding was calculated using the equation: [% G (or Fkn) 293-CX3CR1]-[% G (or Fkn) 293]/[% Fkn (10 nM) 293-CX3CR1]-[% Fkn (10 nM) 293], where G=G glycoprotein, Fkn=fractalkine, 293-CX3CR1=CX3CR1-transfected 293, 293=untransfected 293. The concentration of G glycoprotein was estimated using a molecular weight of 90 kD.

TABLE 2

Percent inhibition of G glycoprotein and Fkn binding to 293-CX3CR1 cells by G glycoprotein, Fkn, G glycoprotein, antibodies, peptides RT32, RT33, RT34, Δ + 1, Δ – 1, and different chemokines in the presence and/or absence of heparin.

| | Range of Inhibition (%) | |
|---|---|---|
| Inhibitor | G glycoprotein | Fkn |
| Anti-G glycoprotein monoclonal antibody | 86-92 | 0-4 |
| Anti-CX3CR1 serum | 88-93 | 90-97 |
| Anti-CX3CR1 monoclonal antibody | 88-94 | 88-92 |
| G glycoprotein (1 μM) | — | 50-58 |
| G glycoprotein (10 nM) | — | 32-38 |
| G glycoprotein (100 pM) | — | 5-8 |
| Fkn (1 μM) | 20-34 | — |
| Fkn (10 nM) | 8-15 | — |
| Fkn (100 pM) | 2-5 | — |
| RT33 (1 μM) | 35-42 | 18-27 |
| Δ – 1 (1 μM) | 8-12 | 0-4 |
| Δ + 1 (1 μM) | 16-22 | 0-8 |
| RT32 (1 μM) | 8-14 | 6-12 |
| RT34 (1 μM) | 4-18 | 6-14 |
| Heparin (5 μg/ml) | 78-84 | 57-65 |
| Heparin (5 μg/ml) + Fractalkine (10 nM) | 85-98 | — |
| Heparin (5 μg/ml) + RT33 (1 μM) | 85-94 | 70-80 |
| Heparin (5 μg/ml) + G glycoprotein (10 nM) | — | 80-85 |
| Heparin (5 μg/ml) + G glycoprotein (10 nM) + RT33 (1 μM) | — | 82-90 |
| Heparin (5 μg/ml) + RT32 (1 μM) | 75-82 | 52-66 |
| Heparin (5 μg/ml) + RT34 (1 μM) | 80-85 | 60-64 |
| Heparin (5 μg/ml) + Δ – 1 (1 μM) | 76-82 | 60-67 |
| Heparin (5 μg/ml) + Δ + 1 (1 μM) | 80-88 | 50-65 |
| Normal rabbit sera | 6-10 | 5-14 |
| Rabbit anti-CCR5 sera | 5-12 | 5-12 |
| MIP-2 (10 μM) | 2-8 | 0-4 |
| C10 (10 μM) | 5-8 | 4-8 |
| KC (10 μM) | 0-6 | 4-6 |
| IP-10 (10 μM) | 0-4 | 0-6 |

Inhibition of Fkn and G glycoprotein binding to 293-CX3CR1 cells by treatment with monoclonal antibodies to G glycoprotein or CX3CR1, or treatment with G glycoprotein, Fkn, or G glycoprotein peptides in the presence or absence of heparin as described in Methods. Fkn and G glycoprotein binding to 293-CX3CR1 cells was inhibited using 5-50 μg/ml heparin. The concentration of G glycoprotein was estimated using a molecular weight of 90 kD.

TABLE 3

RSV plaque reduction by G glycoprotein, fractalkine, G glycoprotein peptides, anti-CX3CR1 antibody, stromal cell derived factor-1-alpha (SDF-1α) and/or heparin on Vero cells.

| Treatment | Concentration | plaque inhibition (%) | p-value |
|---|---|---|---|
| G glycoprotein | 100 nM | 61 | 0.01[a] |
| G glycoprotein | 10 nM | 49 | |
| G glycoprotein | 1 nM | 0 | |
| Fkn | 10 nM | 80 | 0.01[b] |
| Fkn | 1 nM | 31 | |
| Fkn | 100 pM | 0 | |
| G glycoprotein + Fkn | 100 nM + 10 nM | 88 | 0.03[c] |
| Δ + 1 | 1 μM | 30 | 0.05[d] |
| Δ – 1 | 1 μM | 0 | |
| RT32 | 1 μM | 2 | 0.10[e] |
| RT33 | 1 μM | 71 | 0.01[f] |
| RT34 | 1 μM | 6 | 0.08[g] |
| Heparin | 5 μg/ml | 66 | 0.01[h] |
| Heparin + G glycoprotein | 5 μg/ml + 100 nM | 98 | 0.02[i] |
| Heparin + Fkn | 5 μg/ml + 10 nM | 97 | 0.02[j] |
| Heparin + RT33 | 5 μg/ml + 1 μM | 92 | 0.03[k] |
| Heparin + RT32 | 5 μg/ml + 1 μM | 64 | 0.10[l] |
| Heparin + RT34 | 5 μg/ml + 1 μM | 70 | 0.10[m] |
| Heparin + Δ + 1 | 5 μg/ml + 1 μM | 58 | 0.10[n] |
| Heparin + Δ – 1 | 5 μg/ml + 1 μM | 68 | 0.10[o] |
| Anti-CX3CR1 antibody | polyclonal | 38 | 0.02[p] |
| Anti-CX3CR1 antibody + heparin | 5 μg/ml | 91 | 0.03[q] |
| Normal rabbit sera | 5 μg/ml | 6 | |
| SDF-1α | 100 nM | 12 | 0.10[r] |
| SDF-1α | 10 nM | 7 | |
| SDF-1α | 1 nM | 5 | |

[a] p value comparing G glycoprotein inhibition to tissue culture media (TCM) inhibition.
[b] p value comparing Fkn inhibition to TCM inhibition.
[c] p value comparing G glycoprotein + Fkn inhibition to G glycoprotein inhibition.
[d] p value comparing Δ + 1 inhibition to TCM inhibition.
[e] p value comparing RT32 inhibition to TCM inhibition.
[f] p value comparing RT33 inhibition to TCM inhibition.
[g] p value comparing RT34 inhibition to TCM inhibition.
[h] p value comparing heparin inhibition to TCM inhibition.
[i] p value comparing heparin + G glycoprotein inhibition to heparin inhibition.
[j] p value comparing heparin + Fkn inhibition to heparin inhibition.
[k] p value comparing heparin + RT33 peptide inhibition to heparin inhibition.
[l] p value comparing RT32 + heparin inhibition to heparin inhibition.
[m] p value comparing RT34 + heparin inhibition to heparin inhibition.
[n] p value comparing Δ + 1 + heparin inhibition to heparin inhibition.
[o] p value comparing Δ – 1 + heparin inhibition to heparin inhibition.
[p] p value comparing anti-CX3CR1 antibody inhibition to normal rabbit sera inhibition.
[q] p value comparing anti-CX3CR1 antibody + heparin inhibition to heparin inhibition.
[r] p value comparing SDF-1α inhibition to TCM inhibition.

RSV plaque reduction following treatment with G glycoprotein, Fkn, G glycoprotein peptides, anti-CX3CR1 antibody, SDF-1-α and/or heparin as described in Methods. Percent inhibition was determined from the mean plaque forming units (pfu) of treated Vero cells over saline-treated Vero cells using a dilution of RSV that would produce 40-80 pfu. p-values were determined using unpaired two-tailed analysis where p<0.05 is significant. The concentration of G glycoprotein was estimated using a molecular weight of 90 kD.

TABLE 4

Location of the CX3C motif in the G glycoprotein.

```
Partial G glycoprotein amino acid sequence:
      171        182   186              201  (amino acid position)
      ...VPCSICSNNPTCWAICKRIPNKKPGKKTTTKP... (SEQ ID NO: 1)

RT32  : VPCSICSNNPTC              (SEQ ID NO: 2)
RT33  :            TCWAICKRIPNK   (SEQ ID NO: 3)
RT34  :                  NKKPGKKTTTKP (SEQ ID NO: 4)
Δ - 1 :            TCWA CKRIPNK   (SEQ ID NO: 16)
Δ + 1 :            TCWAIACKRIPNK  (SEQ ID NO: 17)
```

The location of the CX3C motif (CWAIC) (SEQ ID NO: 12) in the G glycoprotein compared to G glycoprotein peptides outside the CX3C motif (RT32 and RT34), containing the CX3C motif (RT33) or to peptides with an amino acid deletion (Δ−1) or insertion (Δ+1).

TABLE 5

Leukocyte chemotaxis and percent positive CX3CR1 expression for human peripheral blood mononuclear cells chemotactic toward G glycoprotein, Fkn and G glycoprotein peptide RT33 in the presence or absence of peptide RT33.

|  | CX3CR1 Expression (%) | | |
|---|---|---|---|
|  | Upper | Lower | Chemotactic Indices |
| TCM/G glycoprotein | 8-11 | 25-30 | 3.0-3.6 |
| TCM/Fkn | 7-8 | 26-30 | 3.2-3.7 |
| TCM/RT33 | 11-16 | 16-18 | 1.6-2.2 |
| RT33/G glycoprotein | 16-18 | 9-14 | 1.5-2.0 |
| RT33/Fkn | 16-21 | 6-14 | 1.8-2.2 |

Leukocyte chemotaxis and percent positive CX3CR1 expression on human PBMC after a 6 h chemotaxis assay were determined. The percentage of cells positive for CX3CR1 in both upper and lower modified Boyden chambers are shown. Chemotactic indices were determined from the fold increase of leukocyte migration toward the chemoattractant, i.e. Fkn, G glycoprotein or peptide RT33, over the leukocyte migration toward media alone. TCM=tissue culture media.

TABLE 6

| Treatments | Percentage of cells from BAL determined by H&E stain[i] | | | |
|---|---|---|---|---|
|  | Macrophage | PMN | Eosinophil | Lymphocyte |
| G glycoprotein | 68 ± 10 | 22 ± 4 | 0 ± 0 | 10 ± 3 |
| Fractalkine | 71 ± 10 | 16 ± 5 | 0 ± 0 | 10 ± 3 |
| RT32 | 94 ± 5 | 2 ± 2 | 0 ± 0 | 12 ± 4 |
| RT33 | 76 ± 8 | 16 ± 6 | 0 ± 0 | 4 ± 2 |
| RT34 | 86 ± 8 | 8 ± 3 | 0 ± 0 | 8 ± 2 |

| Treatments | Percentage of cells from BAL determined by flow cytometry[j] | | | | | |
|---|---|---|---|---|---|---|
|  | DX5 | RB6-8C5 | CD11b | B220 | CD4 | CD8 |
| G glycoprotein | 9 ± 6 | 10 ± 4 | 12 ± 5 | 5 ± 4 | 8 ± 2 | 4 ± 3 |
| Fractalkine | 17 ± 8 | 10 ± 6 | 12 ± 4 | 6 ± 2 | 16 ± 4 | 6 ± 2 |
| RT32 | 2 ± 1 | 2 ± 2 | 3 ± 2 | 3 ± 2 | 2 ± 2 | 2 ± 2 |
| RT33 | 10 ± 2 | 12 ± 2 | 10 ± 4 | 4 ± 2 | 10 ± 2 | 4 ± 2 |
| RT34 | 6 ± 2 | 6 ± 4 | 3 ± 1 | 4 ± 2 | 6 ± 2 | 3 ± 3 |

[i]BAL cells were fixed and stained with H&E. The percentages of different cells were determined from >200 cells/slide counting two slides for each experiment. The percent cell type represents the median ± SE from two separate experiments.

[j]Flow cytometry was used to determine the percentage of cell types in the BAL at day 2 post-treatment. 10,000 ungated events were analyzed for DX5+, RB6-8C5+, and CD11b+ cells and a lymphocyte gate was used for analyzing B220+, CD4+, and CD8+ cells.

TABLE 7

Intracellular cytokine expression by CD3+ T cells following in vivo peptide treatment

| Day[a] | Cytokine | Total IC cytokine Expressing CD3+ BAL cells (×10³) ± SEM[b] | | | | | |
|---|---|---|---|---|---|---|---|
|  |  | PBS | RT33 | Δ + 1 | Δ − 1 | EYp1 | RT34 |
| 3 | IL-2 | 56 ± 11 | 26 ± 6.5[c] | 15 ± 2.0 | 46 ± 15 | 26 ± 6.0 | 40 ± 8.5 |
|  | IFNγ | 52 ± 10 | 24 ± 5.6 | 18 ± 2.2 | 47 ± 15 | 32 ± 7.3 | 43 ± 9.4 |
|  | TNFα | 58 ± 11 | 28 ± 7.0 | 19 ± 2.5 | 55 ± 17 | 36 ± 8.1 | 57 ± 12 |
|  | IL-4 | 52 ± 10 | 24 ± 6.0 | 18 ± 2.3 | 47 ± 15 | 32 ± 7.2 | 43 ± 9.2 |
|  | IL-5 | 52 ± 10 | 22 ± 5.6 | 23 ± 2.9 | 49 ± 16 | 34 ± 7.7 | 28 ± 8.0 |
|  | IL-6 | 52 ± 10 | 27 ± 6.8 | 21 ± 2.8 | 51 ± 17 | 35 ± 8.0 | 47 ± 10 |
| 5 | IL-2 | 42 ± 7.0 | 9.0 ± 1.1 | 16 ± 5.1 | 11 ± 1.7 | 17 ± 3.6 | 19 ± 2.8 |
|  | IFNγ | 52 ± 8.3 | 8.0 ± 1.0 | 17 ± 5.3 | 10 ± 1.6 | 26 ± 5.4 | 18 ± 2.6 |
|  | TNFα | 37 ± 6.0 | 9.0 ± 1.1 | 21 ± 6.8 | 18 ± 2.7 | 41 ± 8.4 | 27 ± 3.9 |
|  | IL-4 | 39 ± 6.3 | 11 ± 1.3 | 20 ± 6.2 | 13 ± 1.9 | 28 ± 5.6 | 15 ± 2.2 |
|  | IL-5 | 17 ± 2.7 | 12 ± 1.5 | 23 ± 7.2 | 15 ± 2.2 | 32 ± 6.5 | 24 ± 3.5 |
|  | IL-6 | 50 ± 8.0 | 9.0 ± 1.2 | 21 ± 6.5 | 13 ± 2.0 | 19 ± 7.4 | 30 ± 4.4 |
| 7 | IL-2 | 5.5 ± 0.8 | 2.4 ± 0.3 | 7.5 ± 2.2 | 3.5 ± 0.5 | 7.8 ± 1.1 | 7.7 ± 2.6 |
|  | IFNγ | 7.6 ± 1.1 | 3.6 ± 0.5 | 5.6 ± 1.6 | 4.7 ± 0.7 | 18 ± 2.6 | 10 ± 3.5 |
|  | TNFα | 11 ± 1.6 | 13 ± 0.8 | 15 ± 2.9 | 12 ± 0.7 | 6.8 ± 2.8 | 31 ± 5.0 |

TABLE 7-continued

Intracellular cytokine expression by CD3+ T cells following in vivo peptide treatment

| Day[a] | Cytokine | Total IC cytokine Expressing CD3+ BAL cells (×10³) ± SEM[b] | | | | | |
|---|---|---|---|---|---|---|---|
| | | PBS | RT33 | Δ + 1 | Δ − 1 | EYp1 | RT34 |
| | IL-4 | 7.2 ± 1.1 | 2.3 ± 0.3 | 5.8 ± 1.7 | 2.8 ± 0.4 | 12 ± 1.6 | 11 ± 3.6 |
| | IL-5 | 7.6 ± 1.1 | 5.2 ± 0.7 | 9.9 ± 2.9 | 4.2 ± 0.6 | 20 ± 2.8 | 8.7 ± 2.9 |
| | IL-6 | 6.6 ± 1.0 | 5.8 ± 0.8 | 11 ± 3.3 | 6.3 ± 1.0 | 17 ± 2.4 | 8.9 ± 3.0 |
| 14 | IL-2 | 6.9 ± 1.0 | 3.0 ± 1.0 | 10 ± 3.2 | 8.7 ± 1.0 | 5.1 ± 0.3 | 5.4 ± 1.9 |
| | IFNγ | 7.7 ± 2.8 | 6.5 ± 2.1 | 11 ± 3.5 | 10 ± 1.2 | 5.3 ± 0.3 | 9.7 ± 1.5 |
| | TNFα | 12 ± 4.6 | 8.7 ± 2.6 | 15 ± 4.7 | 11 ± 1.4 | 6.8 ± 0.5 | 10 ± 1.6 |
| | IL-4 | 8.8 ± 3.2 | 8.2 ± 2.7 | 14 ± 4.2 | 12 ± 1.4 | 5.4 ± 0.3 | 8.2 ± 1.3 |
| | IL-5 | 9.4 ± 3.4 | 5.3 ± 1.7 | 16 ± 4.9 | 14 ± 1.7 | 7.7 ± 0.5 | 10 ± 1.7 |
| | IL-6 | 9.4 ± 3.4 | 4.7 ± 1.5 | 12 ± 3.7 | 13 ± 1.6 | 5.0 ± 0.3 | 11 ± 1.7 |

Table 7 Legend
[a] BALB/c mice were treated with PBS, RT33, RT34, Δ + 1, Δ − 1 and EYp1 peptides 24 hours prior to RSV infection. BAL samples from three mice per group were examined for intracellular cytokine expression at days 3, 5, 7 and 14 pi. The results are representative of three independent experiments.
[b] Data are represented as total CD3+ BAL cells expressing IL-2, -4, -5, -6, -IFNγ, TNFα per lung ± SEM (as described in the Materials and Methods).
[c] Values in bold type are statistically different ($p < 0.5$) than corresponding values from PBS-treated mice.

What is claimed is:

1. A method of blocking or inactivating a respiratory syncytial virus G glycoprotein CX3C motif in a subject, comprising administering to said subject a blocking antibody that binds the respiratory syncytial virus G glycoprotein at an epitope sufficiently proximal to the respiratory syncytial virus G glycoprotein C3XC motif to sterically block binding of said G glycoprotein to a CX3C receptor.

2. The method of claim 1 wherein said blocking antibody blocks the biological activity associated with respiratory syncytial virus G glycoprotein binding to a CX3C receptor.

3. The method of claim 1 wherein said blocking antibody alters a secondary structure of the CX3C motif of the respiratory syncytial virus G glycoprotein.

4. A method of treating respiratory syncytial virus (RSV) in a human infected with RSV comprising administering to said human a blocking antibody that binds the respiratory syncytial virus G glycoprotein at an epitope sufficiently proximal to the respiratory syncytial virus G glycoprotein C3XC motif to sterically block binding of said G glycoprotein to a CX3C receptor.

5. The method of claim 4, wherein said antibody is a humanized antibody.

6. A method of protecting a human from respiratory syncytial virus (RSV) infection comprising administering to said human a blocking antibody that binds the respiratory syncytial virus G glycoprotein at an epitope sufficiently proximal to the respiratory syncytial virus G glycoprotein C3XC motif to sterically block binding of said G glycoprotein to a CX3C receptor.

7. The method of claim 6, wherein said antibody is a humanized antibody.

8. A method of blocking or inactivating a respiratory syncytial virus G glycoprotein CX3C motif in a subject comprising: administering a composition comprising a blocking molecule that inhibits the biological activity of a CX3C motif of a respiratory syncytial virus G glycoprotein, wherein the blocking molecule is a peptide that binds to the CX3C receptor, wherein the peptide is selected from the group consisting of: a peptide consisting of VPCSICSNNPTCWAICKRIPNKKPGKKTTTKP (SEQ ID NO: 1), and a peptide comprising TCAAACKRIPNKK (SEQ ID NO: 5).

9. A method of blocking or inactivating a respiratory syncytial virus G glycoprotein CX3C motif in a subject comprising: administering a composition comprising a blocking molecule that inhibits the biological activity of a CX3C motif of a respiratory syncytial virus G glycoprotein, wherein the blocking molecule is a peptide that binds to the CX3C receptor, wherein the peptide is selected from the group consisting of: a peptide consisting of VPCSICSNNPTCWAICKRIPNKKPGKKTTTKP (SEQ ID NO: 1) or a fragment thereof, and a peptide comprising TCAAACKRIPNKK (SEQ ID NO: 5), wherein the peptide fragment of VPCSICSNNPTCWAICKRIPNKKPGKKTTTKP (SEQ ID NO: 1) comprises TCWAICKRIPNK (SEQ ID NO: 3).

* * * * *